United States Patent
Grierson et al.

(10) Patent No.: US 7,371,742 B2
(45) Date of Patent: May 13, 2008

(54) PORPHYRIN DERIVATIVES FOR PHOTODYNAMIC THERAPY

(75) Inventors: David Grierson, Versailles (FR); Philippe Maillard, Saint-Cyr-l'Ecole (FR); Bernard Loock, Villebon-sur-Yvette (FR); Telmo Figueiredo, Paris (FR); Alain Croisy, Cernay-la-Ville (FR); Danielle Carrez, Marly-le-Roi (FR)

(73) Assignees: Institut Curie, Paris (FR); Centre National de la Recherche Scientifique (CNRS), Paris (FR)

( * ) Notice: Subject to any disclaimer, the term of this patent is extended or adjusted under 35 U.S.C. 154(b) by 366 days.

(21) Appl. No.: 10/484,529

(22) PCT Filed: Jul. 18, 2002

(86) PCT No.: PCT/IB02/03364

§ 371 (c)(1),
(2), (4) Date: Jul. 20, 2004

(87) PCT Pub. No.: WO03/008430

PCT Pub. Date: Jan. 30, 2003

(65) Prior Publication Data

US 2004/0259810 A1    Dec. 23, 2004

(30) Foreign Application Priority Data

Jul. 19, 2001 (EP) .................................. 01401936

(51) Int. Cl.
*C07B 47/00* (2006.01)
*C07D 487/22* (2006.01)

(52) U.S. Cl. ............ 514/185; 540/121; 540/145; 514/410; 424/9.362; 424/9.61; 534/15

(58) Field of Classification Search ............ 424/9.362, 424/9.61; 540/145, 121; 534/15; 514/185, 514/410
See application file for complete search history.

(56) References Cited

FOREIGN PATENT DOCUMENTS

| FR | 2709491 | 3/1995 |
|---|---|---|
| FR | 2709491 A1 * | 3/1995 |

OTHER PUBLICATIONS

Ahmad et al. Involve,emt of retinoblastoma (Rb) and E2F transcription factors during photodynamic therapy of human epidermoid carcinoma cells A431. Oncogene (1999) 18, pp. 1891-1896.*
Berg et al. CAS registry and reference. Mitotic inhibition by phenylporphines and tetrasulfonated aluminum phthalocyanine in combination with light. Photochemistry and Photobiology (1992), 56(3) pp. 333-339.*
Guo et al . CAS registry and reference. Synthesis of glycoconjugated metalloporphyrins and their selective catalysis for alkaqne oxidation under mild conditions. Huaxue Xuebao (2000) 58(3) pp. 332-337.*
Pasetto et al. Synthesis of hydrolytically stable porphyrin C- and S-glycoconjugates in high yields. Chemical Communications (2001) pp. 81-82.*
Zhang et al. Synthesis of acetylglycosylated metalloporphyrins and their catalysis for cyclohexane oxidation with PhIO under mild conditions. J. of Molecular Catalysis (2000) 154 pp. 31-38.*
"Synthesis of hydrolytically stable porphyrin C-and S-glycoconjugates in high yields", P. Pasetto, et al. Chem. Commun. (Cambridge), 2001, 81-82.
"Phytodynamic therapy of experimental introcular retinoblastomas-dose-response relationships to light energy and Photofrin II", J. Winther, et al., Acta Ophthalmologica 1989, pp. 44-50.

* cited by examiner

*Primary Examiner*—James O. Wilson
*Assistant Examiner*—Paul V. Ward
(74) *Attorney, Agent, or Firm*—Blakely Sokoloff Taylor & Zafman

(57) ABSTRACT

This invention relates to porphyrin compounds used to destroy or impair the functioning of a target biological material in photodynamic therapy, in particular against virus, tumoral cells, bacteria, tumorous tissues. The invention also relates to compositions containing such compounds and to a method in vitro to photosensitize detroy or impair the functioning of such target biological material.

17 Claims, No Drawings

PORPHYRIN DERIVATIVES FOR PHOTODYNAMIC THERAPY

The present patent application is a non-provisional application of International Application No. PCT/IB02/03364, filed Jul. 18, 2002.

The invention relates to new porphyrin derivatives, their preparation process, their use in photodynamic therapy.

Photodynamic therapy is based on the action of light on certain chemicals called photosensitizers. These light-sensitive molecules accumulate in tumours through uptake mechanisms that are not well understood. When illuminated, the photosensitizers unleash reactive species that can kill cancer cells.

According to the generally accepted mechanism of action, when most photosensitizers are illuminated by light of the correct wavelength and power, they absorb energy that they, in turn, transfer to oxygen, which ordinarily exists in the triplet electronic state.

The energy transferred by the photosensitizer converts triplet oxygen to singlet oxygen, an extremely reactive species that is destructive to cells.

In photodynamic therapy, the tissues that are meant to be destroyed are selectively illuminated and the damage is confined only to those areas. Other sites are not affected, both because the photosensitizers have no toxicity in the absence of light and because they tend to accumulate in the target tissues.

So far, one photosensitizer—called Photofrin® (porfimer sodium)—has gained regulatory approval for photodynamic therapy of any kind.

To date, Photofrin® is used for treatment of esophageal cancer, lung cancer, bladder cancer, gastric and cervical cancers. Furthermore, it is in clinical trials in several countries for treatment of head and neck cancer, as well as Barrett's esophagus. This latter disease is a precancerous condition that could lead to esophageal cancer. It is caused by acid reflux, which may be triggered by stress.

In a typical treatment of cancerous tumours with Photofrin®, the patient receives an intravenous injection of the photosensitizer as an outpatient and then waits for 24 to 48 hours. This waiting period allows the drug to accumulate in the tumour and to be removed from normal tissues. The patient returns to the clinic after the waiting period and the tumour is illuminated for 10 to 30 minutes, often using fiber optics. The patient goes home the same day. However, there is one side effect: Photofrin® stays in the skin for approximately 30 days after treatment, making the patient sensitive to strong light.

Progress has been made. One area where improvement is being sought is light penetration. Light penetrates deeper into tissues as its wavelength increases. In its current applications, Photofrin® is activated at 630 nm.

With tumours, for example, Photofrin®'s effect penetrates through only a few millimetres. A photosensitizer that can be excited at longer wavelengths will penetrate more deeply, reaching further into the tumour.

A second-generation compound described in WO98/50386—benzoporphyrin derivative monoacid ring A, or Verteporfin— has several advantages over Photofrin®. It is activated at 690 nm and thus it can be used to treat more deeply seated or larger tumours than is possible with Photofrin®. It builds up rapidly in target tissues and clears swiftly from normal tissues, allowing light treatment to begin within five minutes after the drug is introduced, compared with the two-day waiting period for Photofrin®V. The rapid uptake and clearance also keep photosensivity to a much shorter period—one day compared with several weeks for Photofrin®. But there are still problems of selectivity towards tumoral cells, of low absorption of red light which is the most penetrating light in biological tissues, and of elimination of the compounds from normal tissues, leading to search for new derivatives.

Strong efforts have been made in order to discover new photosensitizers, which may be photoactivated in the red parts of the visible spectra (example: phthalocyanine, chlorin, benzoporphyrin), which are more selective of tumoral tissues or (and) which are eliminated more quickly by normal tissues. But the problems are not solved.

In a short period, photodynamic therapy has progressed from oncology to ophthalmology, cardiology and dermatology. Applications in urology (enlarged prostate and prostate cancer) and gynaecology (dysfunctional uterine bleeding) also are being examined.

Document WO99/26947 provides for therapeutic macrocycle compounds useful in photodynamic therapy based on a chlorin ring system, stabilized against oxidation by the attachment to the chlorin ring of a structure that comprises one or more exocyclic rings that contributes at least one nitrogen atom.

Besides, document FR 2,709,491 relates to porphyrin derivatives which comprise tetrapyrrolic nucleus substituted meso by at least one phenyl-O-glycosylated group providing an hydrophilic character, other meso positions being preferentially occupied by one, two or three groups with hydrophobic character. These compounds exhibit an amphiphilic character allowing a better transport through the lipidic membrane of cells.

In the last years, a program of synthesis of tetrapyrrolic glycoconjugated neutral photosensitizers, has been developed (Momenteau et al., 1999), in order to obtain more efficient compounds which are water soluble and exhibit various hydrophobicity, in order:

to modulate their transport in the blooded circuit, their interaction with membranous systems of tumoral cells and their cellular localisation to get an active cellular incorporation mechanism, implying lectin receptors.

It is an object of the present invention to identify glycoconjugated compounds with high phototoxic activity, higher than the one known for hematoporphyrin derivatives (HpD or Photofrin®).

It is an other object of the invention to identify compounds which exhibit photocytotoxic effects towards human tumoral cell lines.

It is an other object to provide a method allowing to treat and/or detect cancerous tissue with photodynamic therapy using these compounds.

In accordance with the objects cited the invention relates according to a first aspect to a new porphyrin compound of formula I

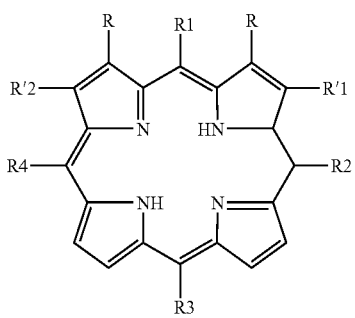

And the metallated and/or labelled and/or conjugated forms thereof wherein,
a) R1=X1-R5, R2=X1-R6, R3=X1-R7, R4=X1-R8
Wherein X1=

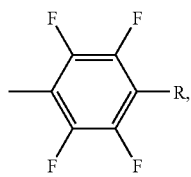

and
a.1) at least one group among R5,R6,R7,R8 is a group A=S-Sugar OH, the other group(s) being the atom F, the sugar being a mono, a di or a polysaccharides, advantageously chosen in the group consisting of maltose, lactose, mannose, and xylose, glucose, or
a.2) at least one group among R5,R6,R7,R8 is A'=O-sugar, the other groups being the atom F, the sugar being a mono, or a polysaccharides, advantageously chosen in the group consisting of galactose, mannose, xylose, glucose, ,or
b) R2=—Y1-H and R=R3=R4=Y1-R9 where Y1=

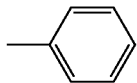

and is substituted in ortho, meta or para, and
b.1) R9=OCH2CH2CH2-S-sugar, the sugar being a mono, a di or a polysaccharides, advantageously chosen in the group consisting of lactose, mannose, glucose and mannose, or
b.2) R9=O—CH2-CH2-Y—CH2-CH2-X-Sugar, or R9=O—CH2-CH2-Y—CH2—CH2-Y—CH2-CH2-X-Sugar, wherein X=O,S, —CH2— and Y=O—, —CH2-, or
b.3) R9=CH2—X-Sugar where X=O,S,CH2, the sugar being a mono, a di or a polysaccharides, advantageously chosen in the group consisting of mannose, xylose, glucose, galactose, lactose, maltose, ,or
c) R1=R2=R3=R4=-Y1-B where Y1 is

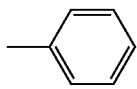

and is substituted in para, and B=(CH2)n-S-sugar, the sugar being a mono or a polysaccharides advantageously mannose, xylose, glucose and n=1 or 2, ,or
d) R1=C-A4, R2=C-A3, R3=C-A2, R4=C-A1 where each substituent C is

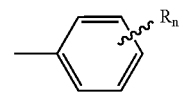

and is a m-hydroxyphenyl or p-hydroxyphenyl and
d.1) at least two groups among A1,A2,A3,A4 are the group O-glucose OH, the others being the atom H, or
d.2) at least two groups among A1,A2,A3,A4 are the group O—CH2CH2CH2-O-glucoseOH, the others being the atom H and wherein R=R'1=R'2=H in a), b), c), d) or
e) R1=R2=R3=H, R=R'1=R'2=CH2CH3 and R4=D-sugar where D=

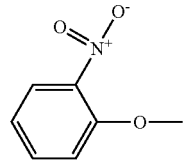

the sugar being a mono or a polysaccharides, advantageously chosen in the group consisting of glucose, maltose, mannose, xylose, or
R1=R2=R3=R4=H, R=CH3, R'1=D-H, R'2=D-sugar the sugar being a mono or a polysaccharides, advantageously chosen in the group consisting of maltose, mannose, xylose, lactose and higher polysaccharides.

Advantageously the invention is related to a compound chosen in the group consisting of the porphyrin derivatives mentioned above wherein
a) R5=R6=R7=R8=S-Sugar OH
b) R5=R7=R8=S-Sugar OH and R6=F
c) R6=R8=S-Sugar OH and R5=R7=F
d) R7=R8=S-Sugar OH and R5=R6=F
where Sugar is a mono or a polysaccharides, advantageously glucose or mannose or xylose.

Advantageously the invention is related to a compound chosen in the group consisting of the porphyrin derivatives mentioned above wherein
a) R5=R6=R7=R8=S-Sugar OH
b) R5=R7=R8=S-Sugar OH and R6=F
where Sugar=xylose Advantageously the invention is related to a compound chosen in the group consisting of the porphyrin derivatives mentioned above wherein
a) R5=R7=R8=S-Sugar OH and R6=F
b) or R6=R8=S-Sugar OH and R5=R7=F
c) or R7=R8=S-Sugar OH and R5=R6=F where Sugar=mannose Advantageously the invention is related to a compound chosen in the group consisting of the porphyrin derivatives mentioned above wherein
  a) A1=A2=A3=A4=O-D-glucose OH
  b) A1=A2=A3=O-D-glucose OH, A4=H
  c) A1=A2=O-D-glucose OH, A3=A4=H Advantageously the invention is related to a compound where A1=A2=A3=A4=O-D-glucose OH.

Among all the compounds mentioned above, the invention relates most preferably to the compounds of table C2 to C7.

According to another aspect the invention relates to the compounds above used as drugs. Pathologies are localised solid tumors namely non-small-cell lung cancer, prostate, oesophageal, skin, breast, bladder and pancreatic cancers, Karposi's sarcoma, ophthalmological diseases as retinoblastoma, age-related macular degeneration (AMD), other diseases as psoriasis, arthritis and photoangioplasty of peripheral arterial disease.

According to another aspect the invention relates to such a compound used to destroy, impair the functioning of a target biological material in photodynamic therapy.

According to another aspect the invention relates to a pharmaceutical composition which comprises an effective amount of a compound mentioned above in admixture with at least one pharmaceutically acceptable excipient.

According to another aspect the invention relates to the use of such a compound for the preparation of a composition useful in photodynamic therapy. According to another aspect the invention relates to a method of photodynamic therapy using at least one of the compounds mentioned above.

According to another aspect the invention relates to the use of such a compound in a method to photosensitive, destroy, impair the functioning of a target biological material, or to detect a tumor in vivo, the method comprising the steps:
  administrate the composition at a person at a concentration of 0.1 to 20 mg/Kg body weight, advantageously 1 to 5 mg/Kg
  irradiate the biological target or the tumor in vivo at a wavelength absorbed by the compound.

According to another aspect the invention relates to a method ex vivo or in vivo to photosensitize, destroy or impair the functioning of target biological material which comprises contacting said target with an effective amount of such a compound and irradiating said target with light at a wavelength absorbed by said compound. The biological material is typically virus, tumoral cells, bacteria, tumorous tissues.

Other features and advantages of the invention will be apparent from the following detailed description.

The invention refers more specifically to the very advantageous compounds shown in table A below. Among the sugar cited in the text, galactose, xylose, glucose, maltose are advantageously β form, and mannose is advantageously a form.

TABLE A

Porphyrin derivatives.

| Compound | | Sugar |
|---|---|---|
| 23 | 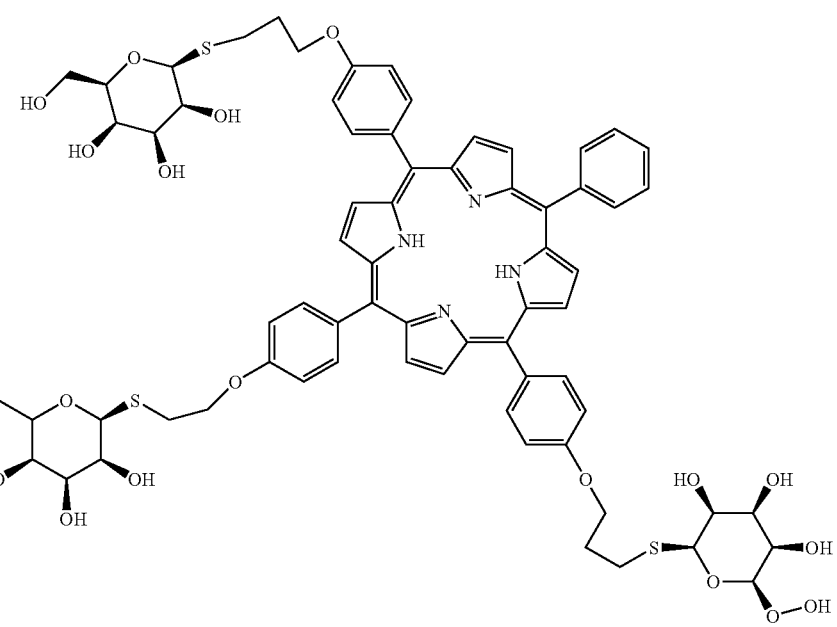 | Thio β-glucose C3 (TPP(p-OC$_3$-S-β-GluOH)$_3$) |

TABLE A-continued

Porphyrin derivatives.

| Compound | | Sugar |
|---|---|---|
| 24 | [structure] | Thio α-Mannose C3 (TPP(p-OC$_3$-S-α-MannOH)$_3$) |
| 25 | [structure] | TPP F$_4$(p-S-β-GluOH)$_4$ |

TABLE A-continued
*Porphyrin derivatives.*
| Compound | | Sugar |
|---|---|---|
| 26 | 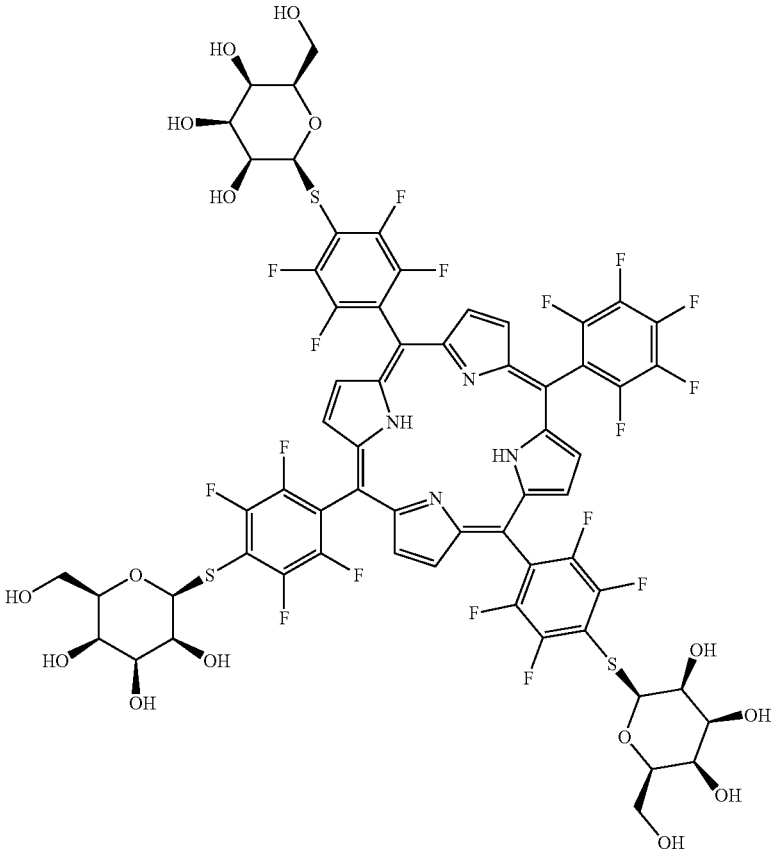 | Thio β-Glucose F4 (TPP F$_4$(p-S-β-GluOH)$_3$) |

TABLE A-continued
Porphyrin derivatives.
| Compound | | Sugar |
|---|---|---|
| 27 | 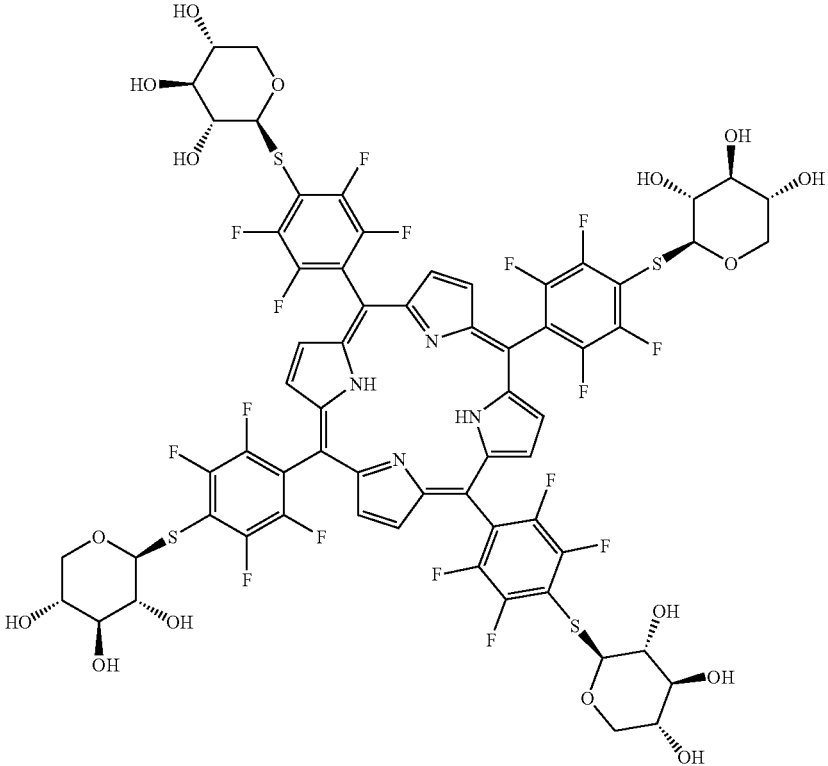 | Thio β-xylose F4 (TPP F$_4$(p-S-β-XylOH)$_4$) |
| 28 | 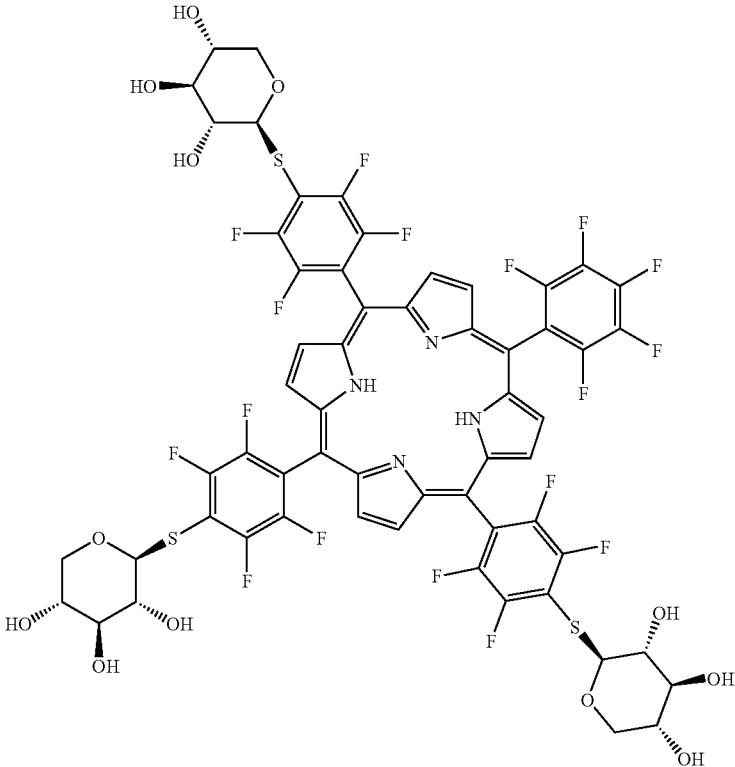 | Thio β-xylose F4 (TPP F$_4$(p-S-β-XylOH)$_3$) |

TABLE A-continued

Porphyrin derivatives.

| Compound | | Sugar |
|---|---|---|
| 29 | | Thio α-mannose F4 (TPP F$_4$(p-S-α-MannOH)$_4$) |
| 30 | | Thio α-mannose F4 |

TABLE A-continued
Porphyrin derivatives.
| Compound | | Sugar |
|---|---|---|
| 31 | 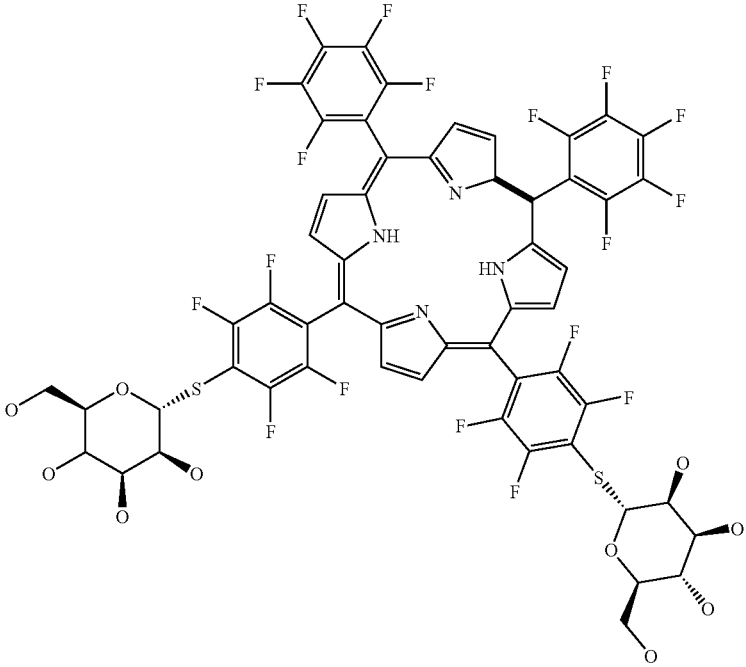 | Thio α-mannose F4 |
| 32 | 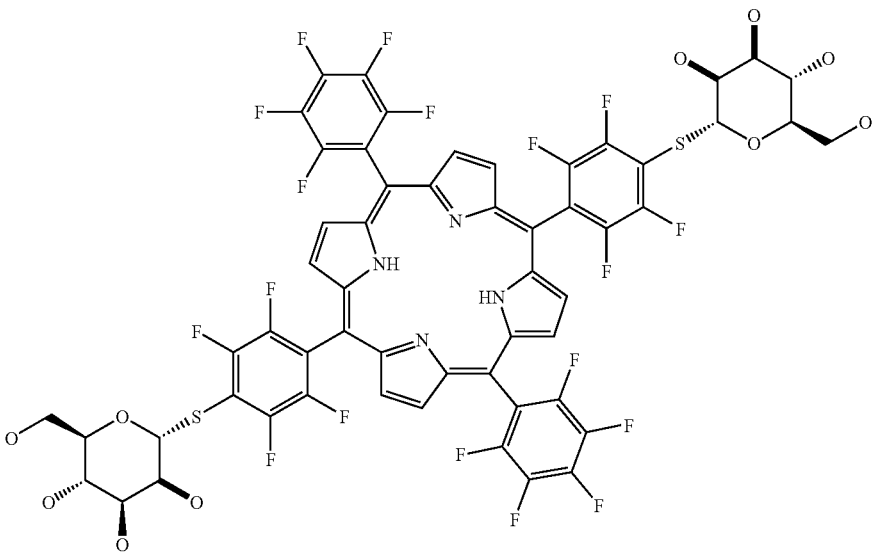 | Thio α-mannose F4 |

TABLE A-continued

Porphyrin derivatives.

| Compound | Sugar |
|---|---|
| 33 | Thio α-mannose F4 (TPP F$_4$(p-S-α-MannOH)$_3$) |

TABLE A-continued

Porphyrin derivatives.

| Compound | | Sugar |
|---|---|---|
| 41 | | β-Lactose |
| 42 | | Porphyrin β-Glucose |
| 43 | | Azaporphyrin β-Glucose |

TABLE A-continued

Porphyrin derivatives.

| Compound | Sugar |
|---|---|
| 44 | Porphyrin β-Maltose |
| 47 | Porphyrin β-Maltose |
| 48 | Azaporphyrin β-Maltose |

TABLE A-continued
Porphyrin derivatives.
| Compound | Sugar |
|---|---|
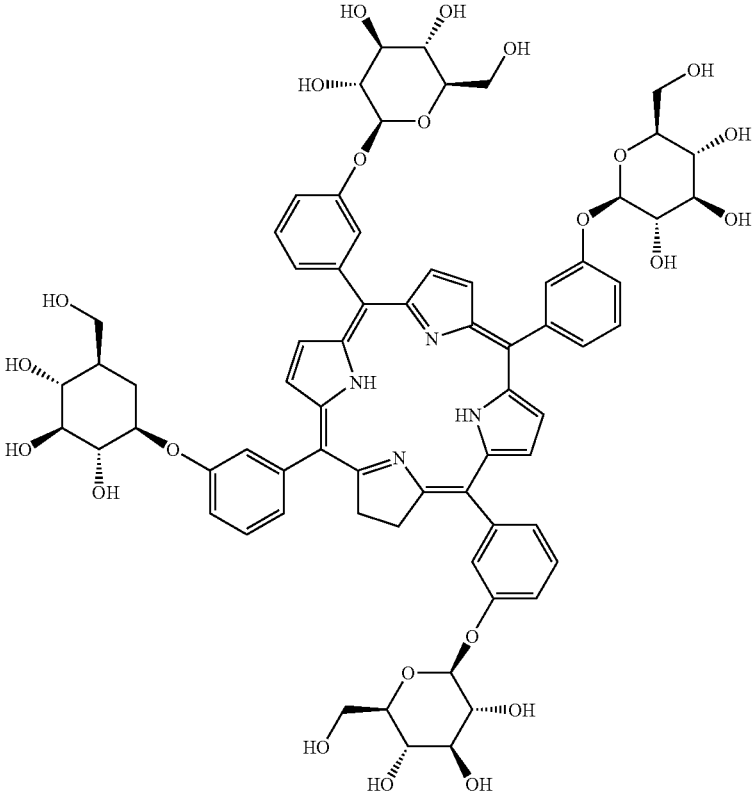
54 — Chlorin β-Glucose (TPC(m-O-β-GluOH)$_4$)

TABLE A-continued
Porphyrin derivatives.
| Compound | | Sugar |
|---|---|---|
| 55 | 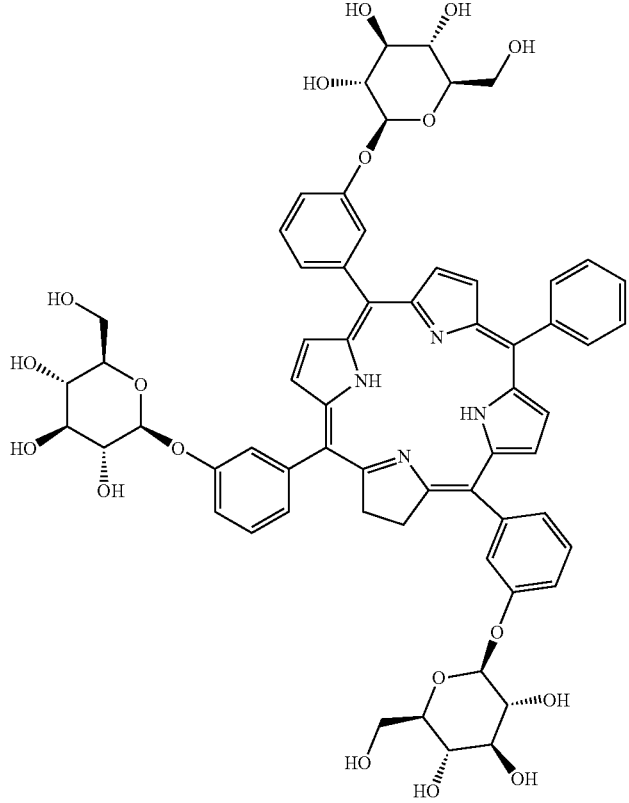 | Chlorin β-Glucose (TPC(m-O-β-GluOH)₃) |
| 56 | 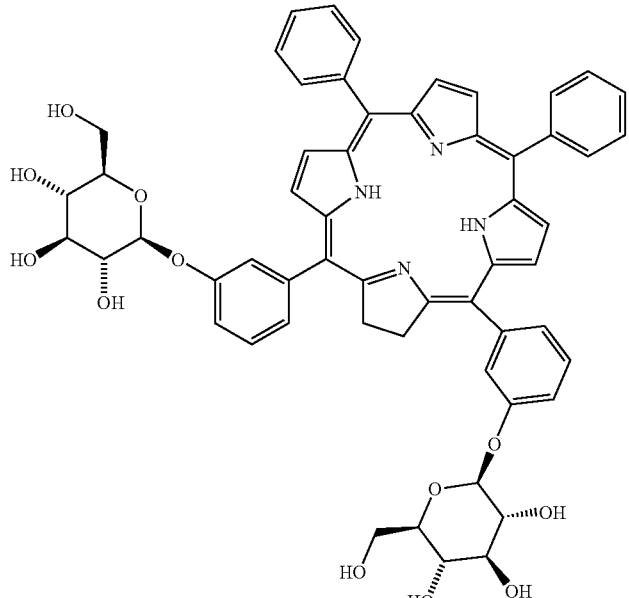 | Chlorin β-Glucose |

TABLE A-continued

Porphyrin derivatives.

| Compound | Sugar |
|---|---|
| 57 | Chlorin β-Glucose |
| 58 | Chlorin β-Glucose C2 |

TABLE A-continued
Porphyrin derivatives.
| Compound | | Sugar |
|---|---|---|
59 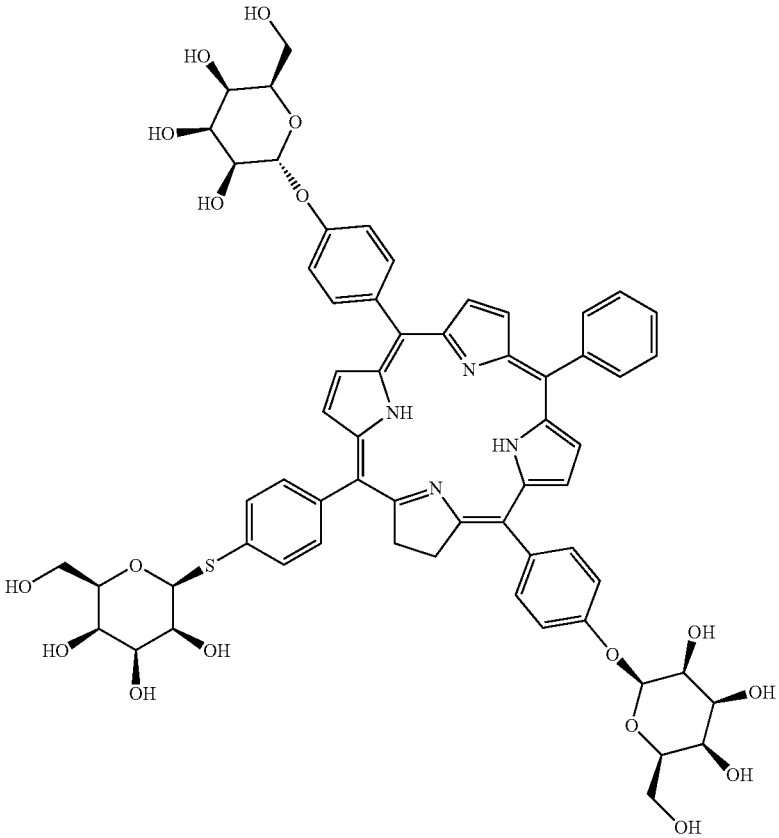 Chlorin
β-Glucose TABLE A-continued Porphyrin derivatives.

| Compound | Sugar |
|---|---|
| 60 | Porphyrin β-Glucose |
| 61 | Porphyrin β-Glucose C2 |

TABLE A-continued

Porphyrin derivatives.

| Compound | Sugar |
|---|---|
| 62 | |
| 63 | β-Glucose |

TABLE A-continued
Porphyrin derivatives.
| Compound | | Sugar |
|---|---|---|
| 64 | 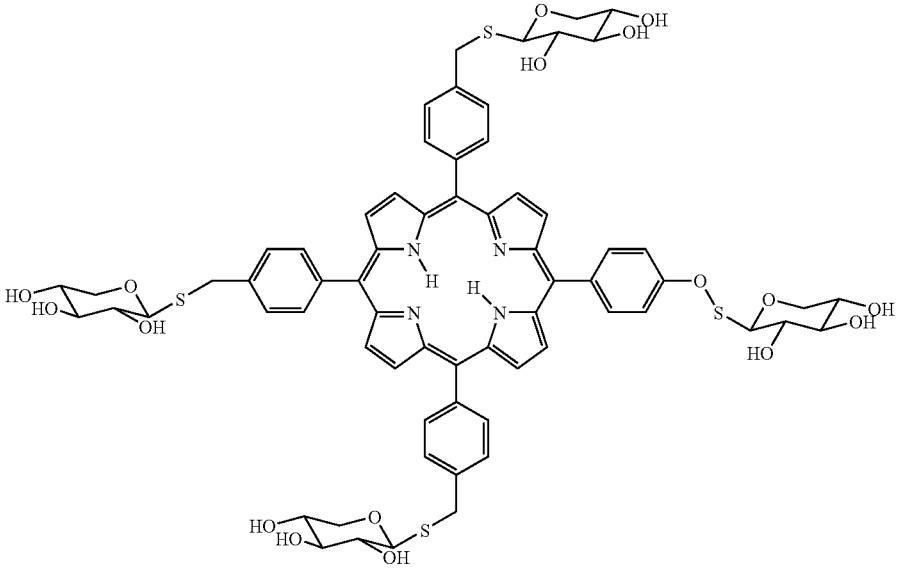 | β-Xylose (TPP(p-CH$_2$-S-β-XylOH)$_4$) |
| 65 | 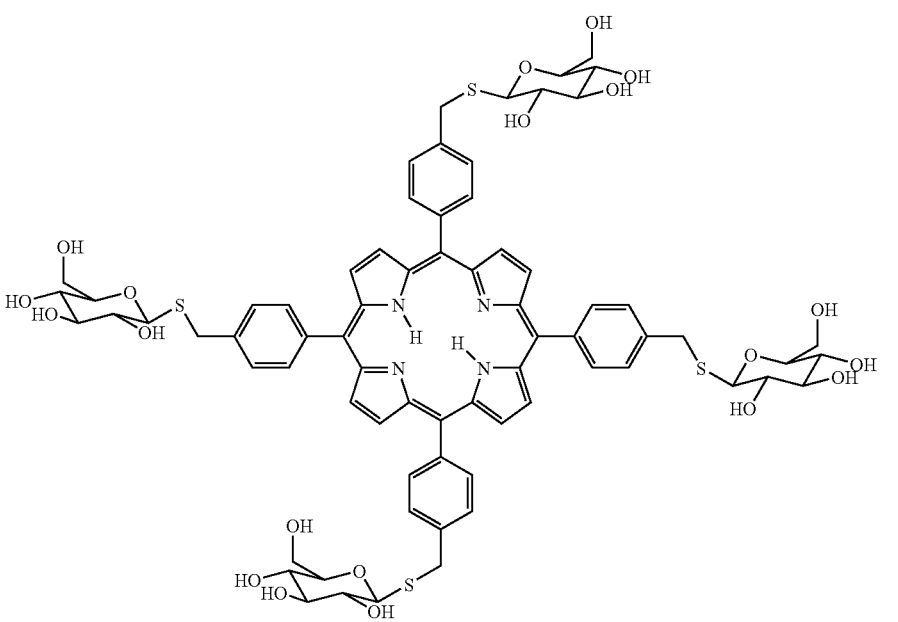 | β-Glucose (TPP(p-CH$_2$-S-β-GluOH)$_4$) |

TABLE A-continued
Porphyrin derivatives.
| Compound | | Sugar |
|---|---|---|
| 66 | 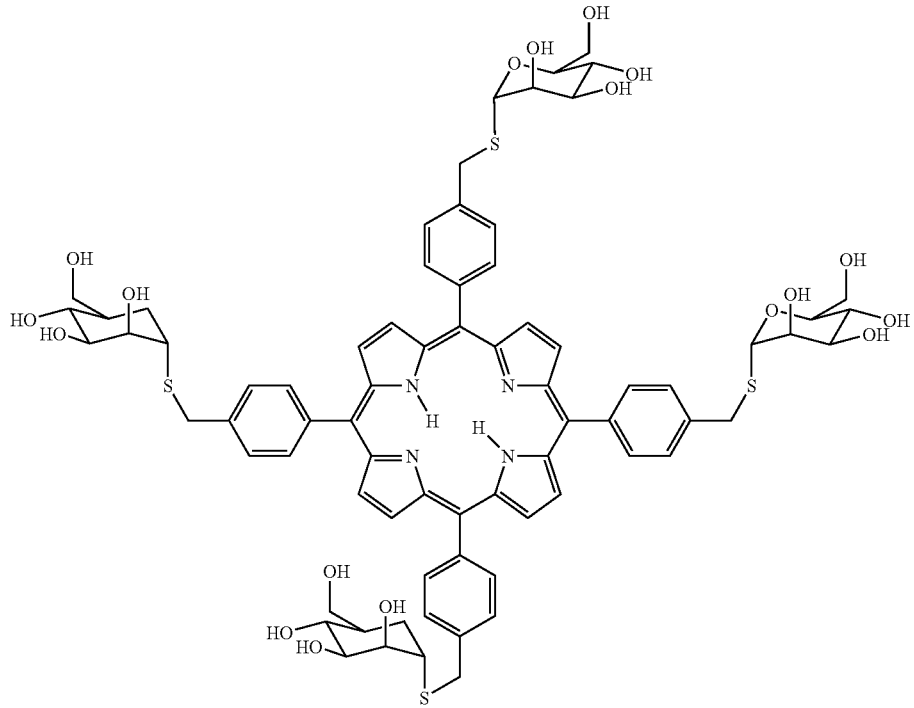 | α-Mannose (TPP(p-CH$_2$-S-α-MannOH)$_4$) |
| 67 | 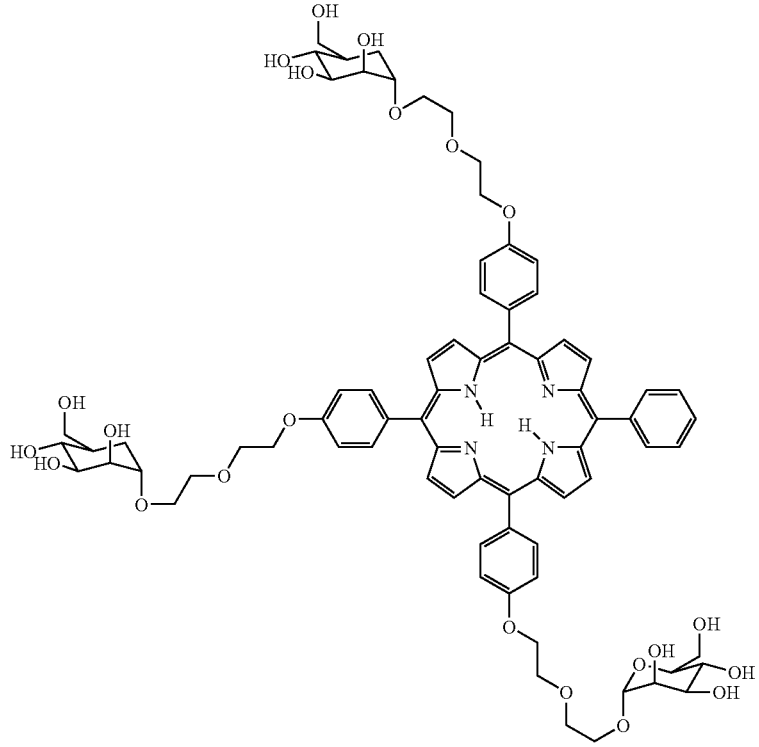 | α-Mannose (TPP(p-O-DEG-O-α-Mann)$_3$) |

TABLE A-continued
Porphyrin derivatives.
| Compound | | Sugar |
|---|---|---|
| 68 | 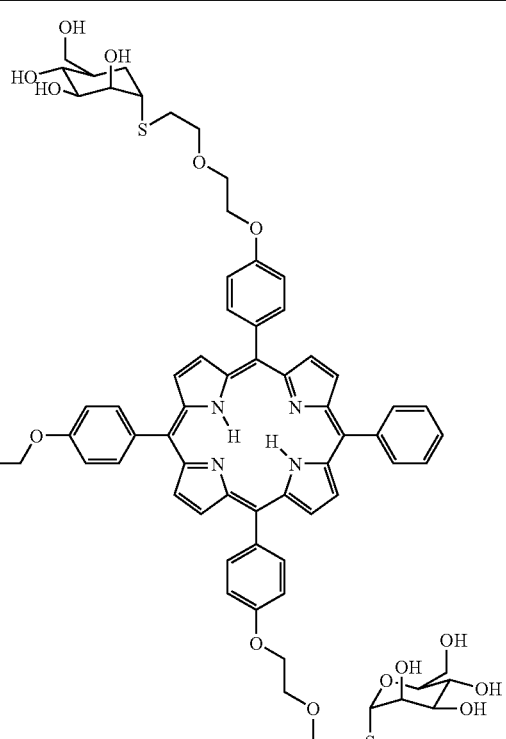 | α-Mannose (TPP(p-O-DEG-S-α-Mann)$_3$ |
| 75 | 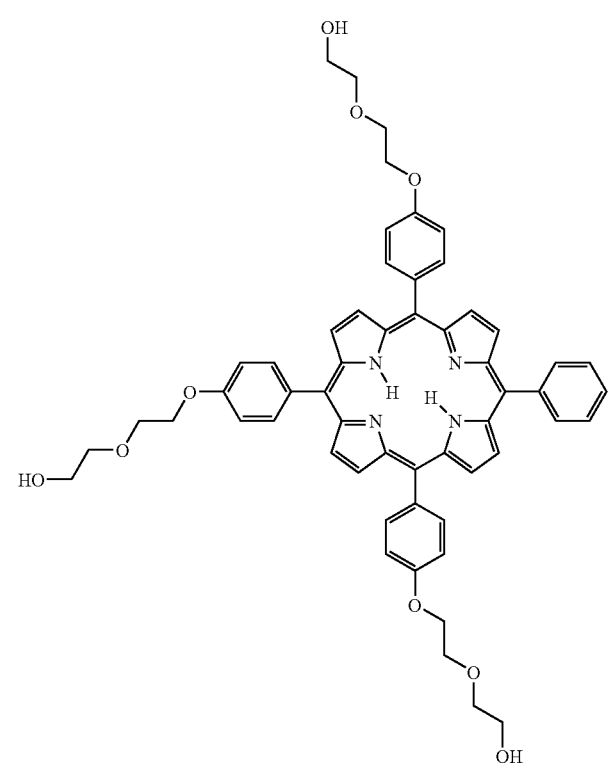 | TPP(p-O-DEG-OH)$_3$ |

TABLE A-continued
Porphyrin derivatives.
| Compound | | Sugar |
|---|---|---|
| 74 | 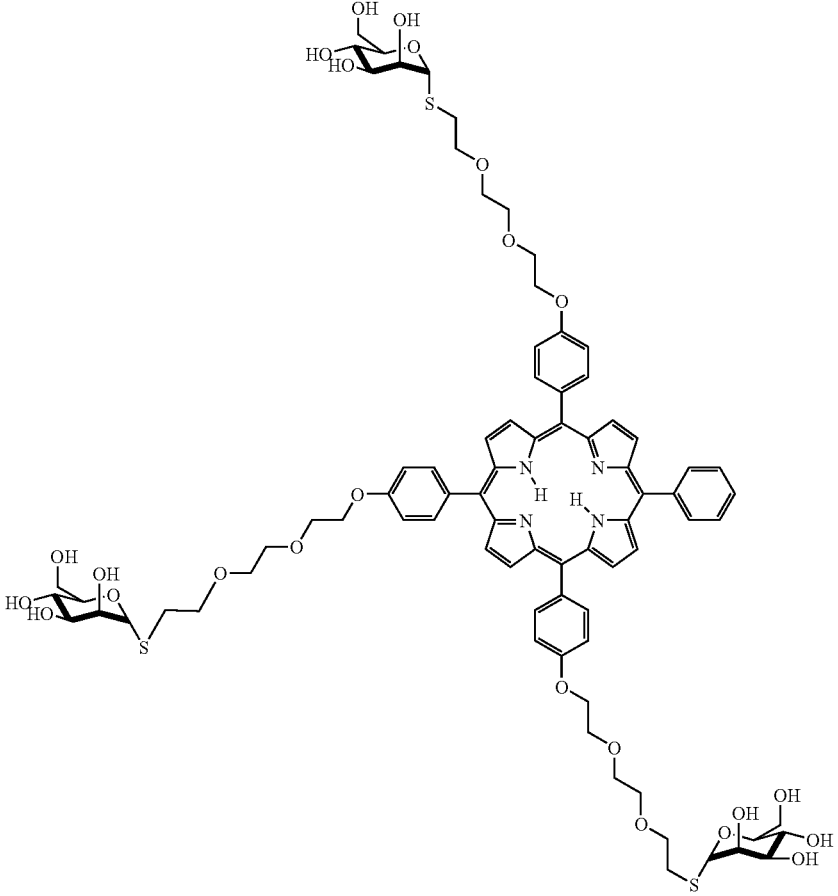 | TPP(p-O-TEG-S-α-MannOH)$_3$ |
| 77 | 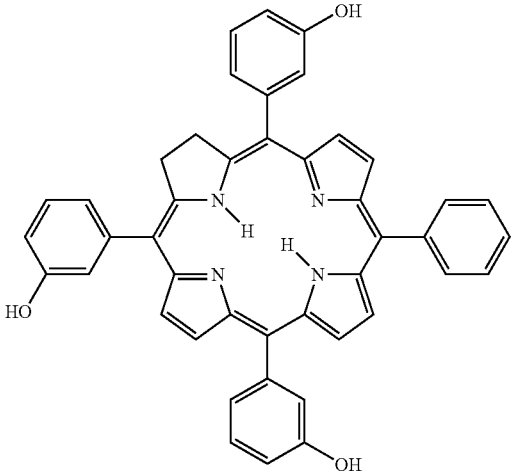 | |

TABLE A-continued
Porphyrin derivatives.
| Compound | | Sugar |
|---|---|---|
| 78 | 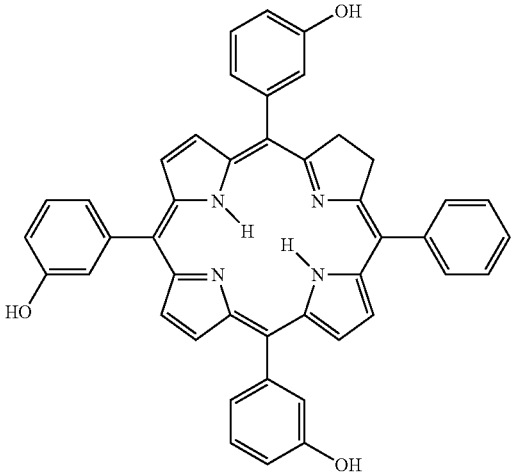 | |
| 71 | 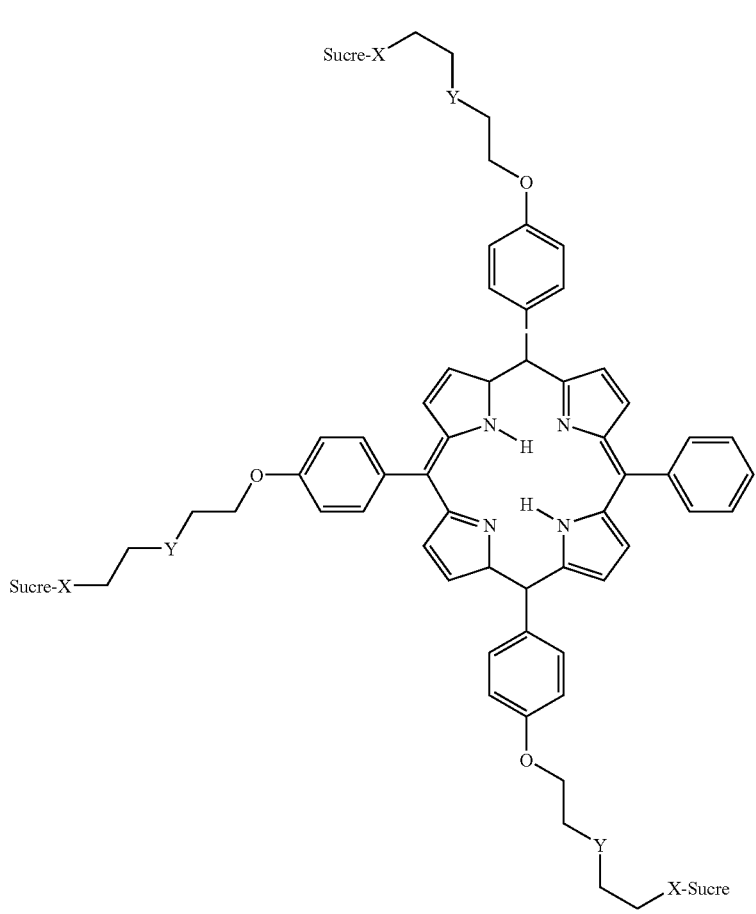 | |
$X = O, S, —CH_2—$
$Y = —O—, —CH_2—$ -continued
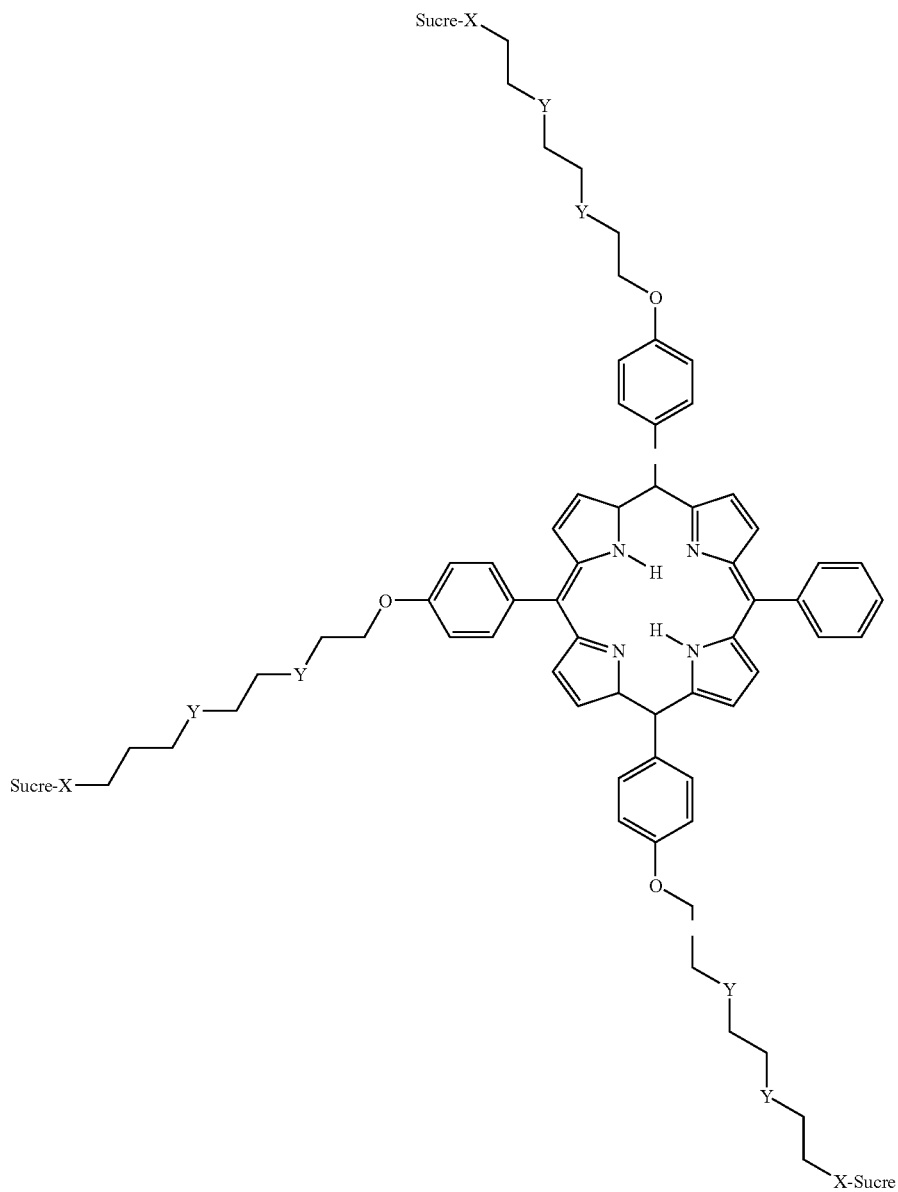
72
Examples of sugar
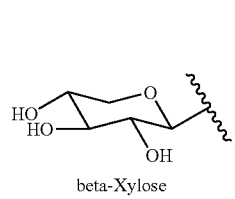
beta-Xylose
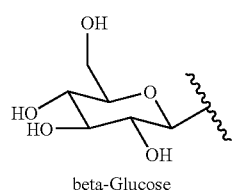
beta-Glucose
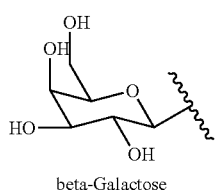
beta-Galactose
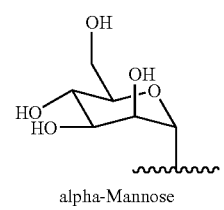
alpha-Mannose

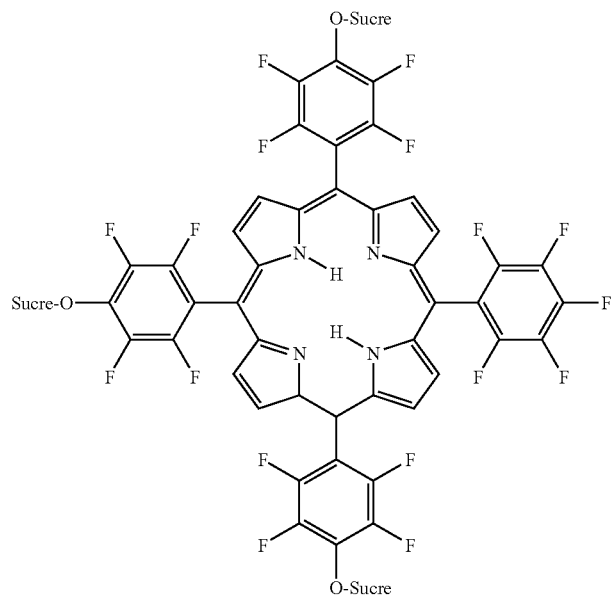
70
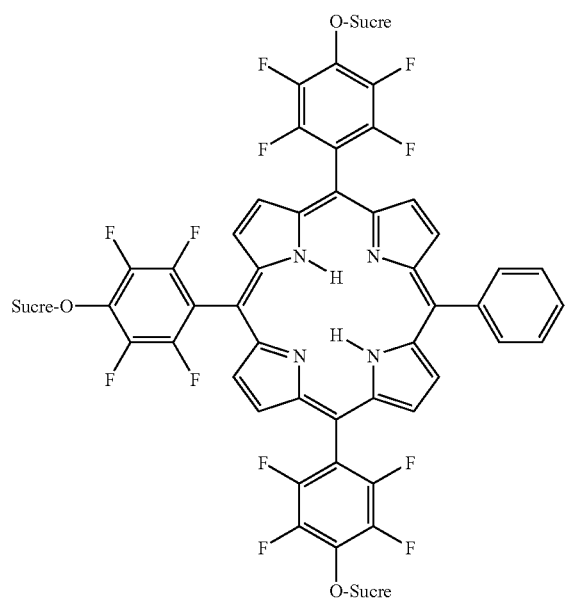
Examples of sugar
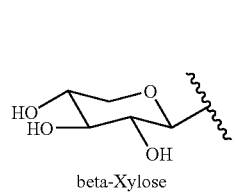
beta-Xylose
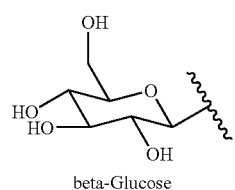
beta-Glucose
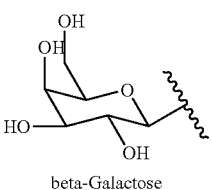
beta-Galactose -continued
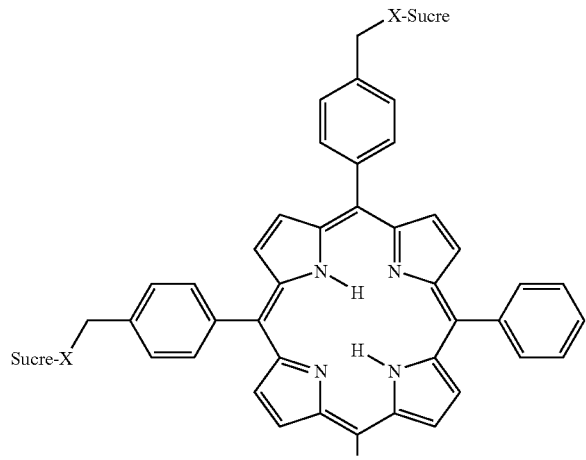
73
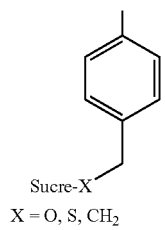
X = O, S, CH₂
Examples of sugar
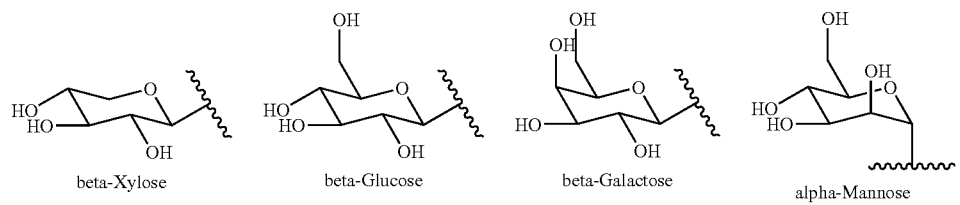
The compound TPC(m-OH)₃ is a mixture of the two isomers 77,78 in equal proportion.
The preparation of some compounds of table A will now be described.
1) Compounds 23-24 are prepared as represented in scheme 1

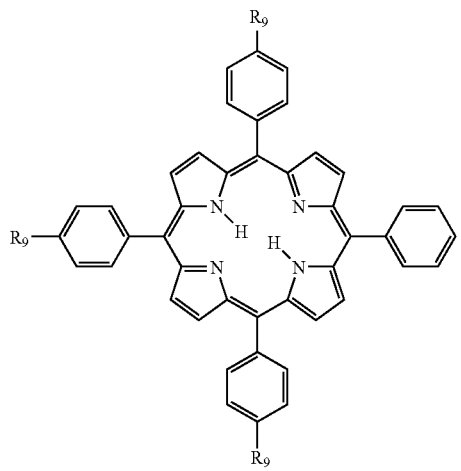

R$_9$ = OCH$_2$CH$_2$CH$_2$Br

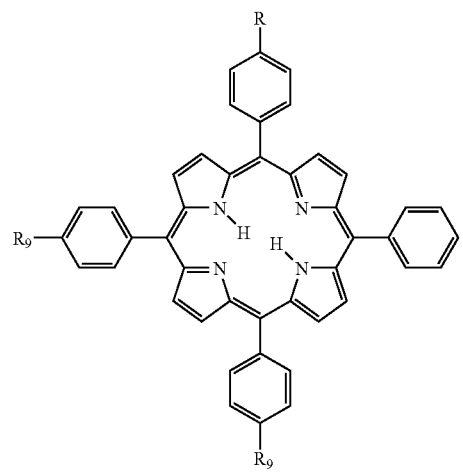

R$_9$ = OCH$_2$CH$_2$CH$_2$—S—Sugar Acetyl

Sugar = β-D-glucose, α-D-mannose, β-D-xylose

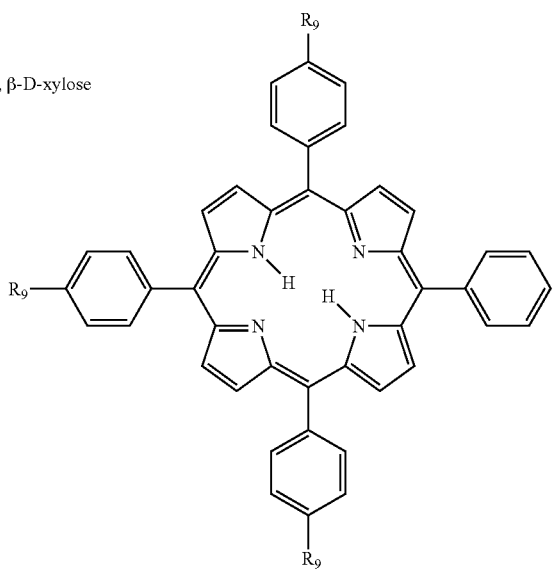

R$_9$ = OCH$_2$CH$_2$CH$_2$—S—Sugar OH

Compound 24 (Glycosylation):

To a solution of 100 mg of porphyrin [5,10,15-tris(bromo-3-propyloxy-4-phenyl)-20-phenyl porphyrin, (9,76 10$^{-5}$ mole)], and 160 mg of α-D-Thio-2,3,4,6-tetraacetyl mannose (0.44 mmol, 4,5 equivalents) in 20 ml of acetone dried on molecular sieve 4 Å was added 60 mg of potassium carbonate (0.44 mmol, 4,5 equivalents). The solution is stirred in the dark for one night under argon and at ambient temperature. The solution is evaporated under vacuum, reused trough dichloromethane, washed twice in distilled water. The organic phase is dried under sodium sulphate, filtered and evaporated under vacuum. The crude product is purified by preparative silica gel chromatography, eluted with a mixture dichloromethane/ether 10/1, v/v. The more polar compound is selected and after recrystallisation of mixture from dichloromethane/heptane. 93 mg (51%) of purple powder is obtained.

Compound 24 (Deacetylation):

50 mg of the previous compound is treated calling to the general protocol precised in reference 16. The compound is obtained after two recrystallisations in a mixture of methanol/1,2-dichloroethane containing a pyridine trace. The unprotected porphyrin is obtained quantitatively.

2) Compounds 26-33 are prepared as represented in schem 2

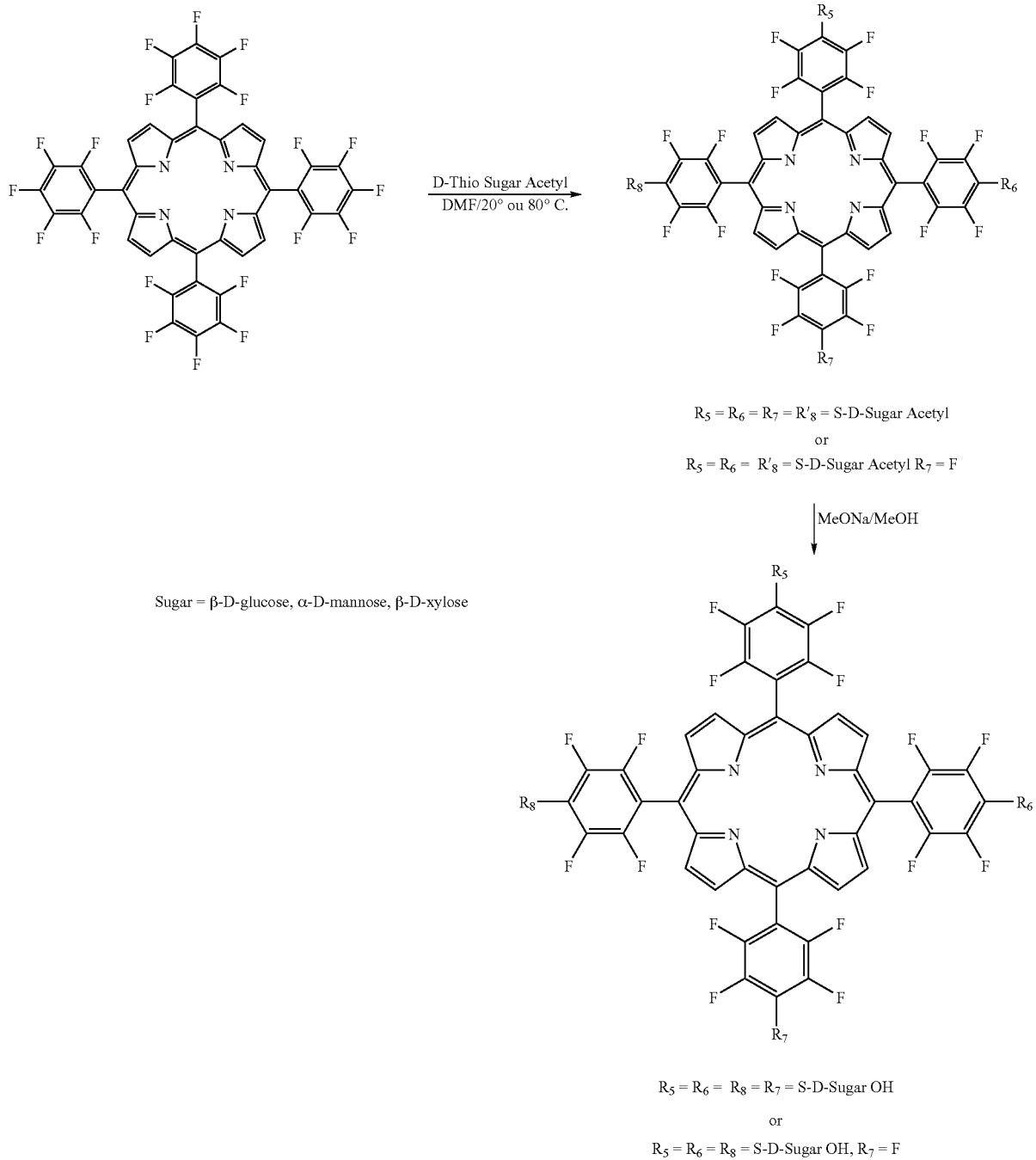

Sugar = β-D-glucose, α-D-mannose, β-D-xylose

Compounds 25 and 26: example of optimisation for a triglycosylated compound

Glycosylation:

Protected Porphyrin:

100 mg of 5,10,15,20-tetrakis (pentafluorophenyl) porphyrin prepared using to the method of Lindsey et al. (Lindsey, J. S; Schreiman, I. C.; Hsu, H. C; Kearney, P. C.; Marguerettaz; A.M.J. Org. Chem. 52,827-836,1987) (0.103 mmol) and 225 mg of β-D-Thio-2,3,4,6-tetraacetyl glucose (0.617 mmol, 1,5 equivalents/F) are dissolved in 25 ml distillated dimethylformamide. The solution is stirred under argon and in the dark for 3 days. The solution is evaporated under vacuum and the residue is dissolved in dichloromethane. The solution is purified by preparative silica gel chromatography, eluted with a mixture of dichloromethane/ether 10/1, v/v. 100 mg (yield. =48%) of compound 26 (protected) (Rf=0,30) and 66 mg (yield=27%) of compound 25 (protected) (Rf=0,10) are obtained after recrystallisation from a mixture of dichloromethane/heptane. Three mono and diglycosylated compounds were obtained as a mixture (yield 25%)

Deacetylation:

50 mg of the previous compound [25(protected) or 26(protected)] are treated according to the general protocol precised in "Tetrapyrrolic glycosylated macrocycles for PDT" M. Momenteau, Ph. Maillard, M. A. de Bélinay, D. Carrez et A. Croisy, J. Biomedical Optics 4 (3),298-318, 1999. After two recrystallisations in a mixture of methanol-1,2-dichloroethane containing pyridine traces, the compound is obtained. The unprotected porphyrin is obtained substantially quantitatively.

Protected Compounds 29 and 31: Examples of Optimisation Towards the Tetraglycosylated Compound Glycosylation:

100 mg of 5,10,15,20-tetrakis (pentafluorophenyl) porphyrin (0.103 mmol) and 225 mg of α-D-Thio-2,3,4,6-tetraacetyl mannose (0.617 mmol, 1,5 equivalents/F) are dissolved in 25 ml of distilled dimethylformamide. The solution is stirred under argon and in the dark for 4 days. The solution is evaporated under vacuum and the residue is dissolved in dichloromethane. The solution is purified by chromatography on silica gel plaque eluted with a mixture of dichloromethane/ether 5/1, v/v. 54 mg (yield=26%) of compound 31 (prot.) (Rf=0,75) and 140 mg (yield=58%) of compound 29 (prot.) (Rf=0,62) are obtained after recrystallisation of a mixture dichloromethane/heptane.

Deacetylation:

50 mg of the previous compound are treated according to the general protocol precised by Zemplen, G. Gerecs, A. Haracsy, C. Ber. 1936, 69, 1827. After two recrystallisations in a mixture of methanol/1,2-dichloroethane containing a trace of pyridine, the compound is obtained. The unprotected porphyrin is obtained substantially quantitatively.

3) Compounds 54-59 are prepared as represented in schem 3:

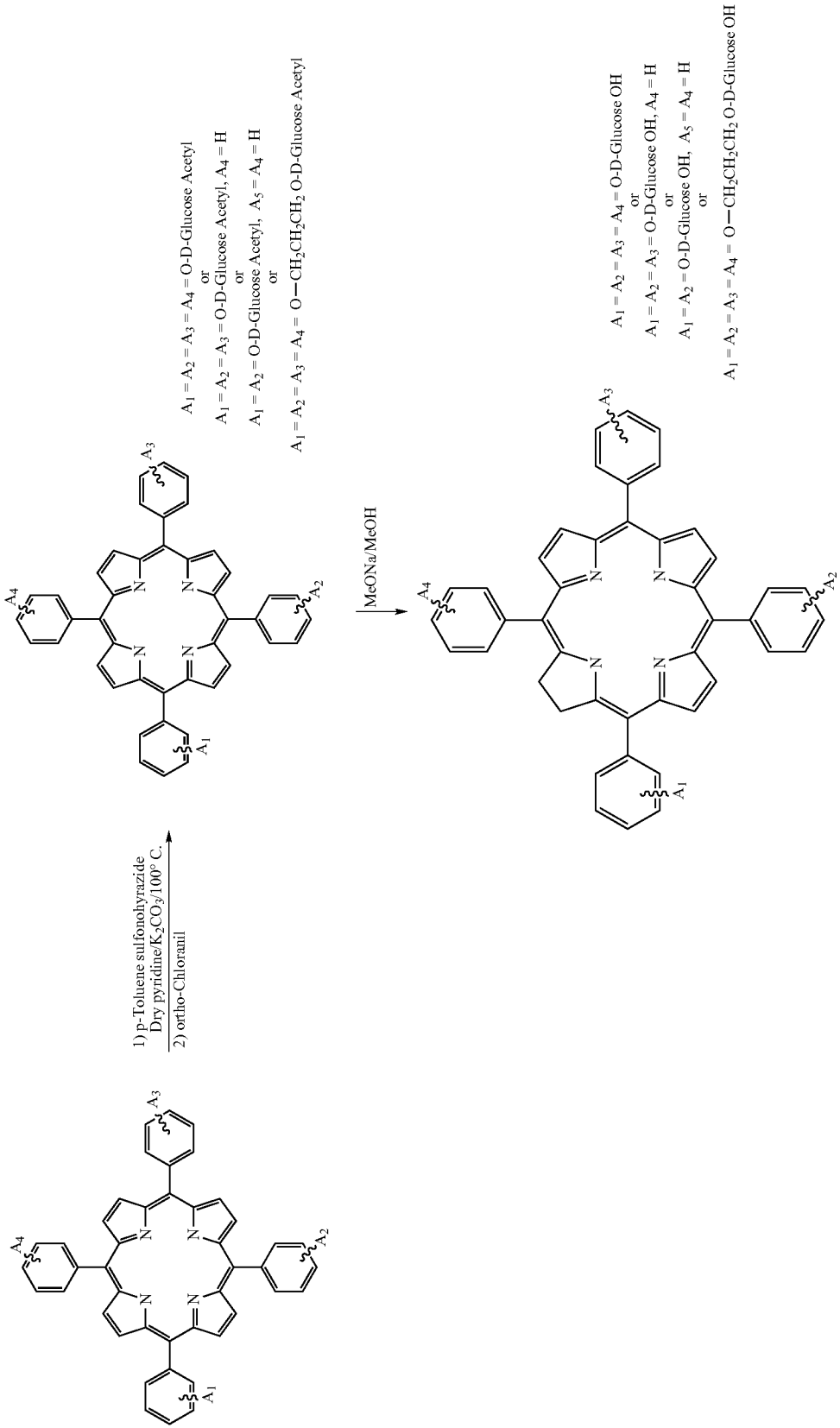

Compound 54:

350 mg of 5,10,15,20-tetrakis (3-O-β-D-2,3,4,6-tetraacetyl glucosyloxyphenyl) porphyrin (0.175 mmol) and 220 mg of potassium carbonate are dissolved in 8 ml of pyridine dried under activated molecular sieve 4 Å and 220 mg $K_2CO_3$ was added. The solution is deoxygenated by argon stream during 20 minutes. 65,6 mg of para-toluene sulphonohydrazide (0.352 mmol, 2 equivalents) are added dissolved in the minimum of dried pyridine. The solution is heated at 100° C. under argon for 6 hours 30. Every 2 hours, 71 mg de para-toluene sulphonohydrazide are added into 0.25 ml of dried pyridine. To the solution cooled at room temperature, 55 ml of ethyl acetate and 22.5 ml of water are added. The mixture is stirred at 100° C. during 1 hour. The mixture is decanted, the aqueous phase is extracted with ethyl acetate. The organic phases are washed with chlorhydric acid 2N, water, saturated solution of sodium bicarbonate and dried under sodium sulphate. The simultaneous presence of chlorin and bacteriochlorin analogues, and the disappearance of porphyrin are verified by UV visible spectroscopy. 121 mg of ortho chloranil (0.5 mmol) are added by small amounts to the organic solution until disappearance of specific UV visible band (735 nm) of bacteriochlorin. The organic solution is washed with sodium hydrogenosulphate (5%), with water then dried under sodium sulphate. The solution is evaporated under vacuum. The crude product is purified by chromatography on silica gel column eluted with a mixture of dichloromethane/acetone 5/1, v/v. After recrystallisation from a mixture of dichloromethane/heptane, 302 mg of crystals are obtained (yield 89%).

Deacetylation:

50 mg of the previous compound are treated according to the general protocol precised in reference "Tetrapyrrolic glycosylated macorcycles for PDT" M. Momenteau, Ph. Maillard, M. A. de Bélinay, D. Carrez et A. Croisy, J. Biomedical Optics 4 (3),298-318,1999. The compound is obtained after two recrystallisations in a mixture of methanol/1,2-dichloroethane containing a pyridine trace. The unprotected chlorin is obtained quantitatively.

4) Compound 68 is prepared as represented in schem 4:

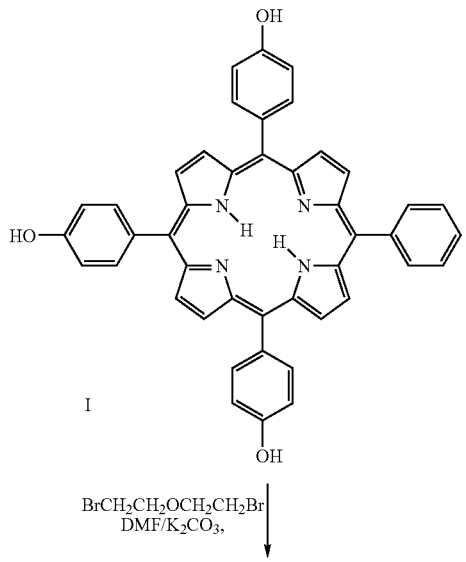

I

BrCH$_2$CH$_2$OCH$_2$CH$_2$Br
DMF/K$_2$CO$_3$,

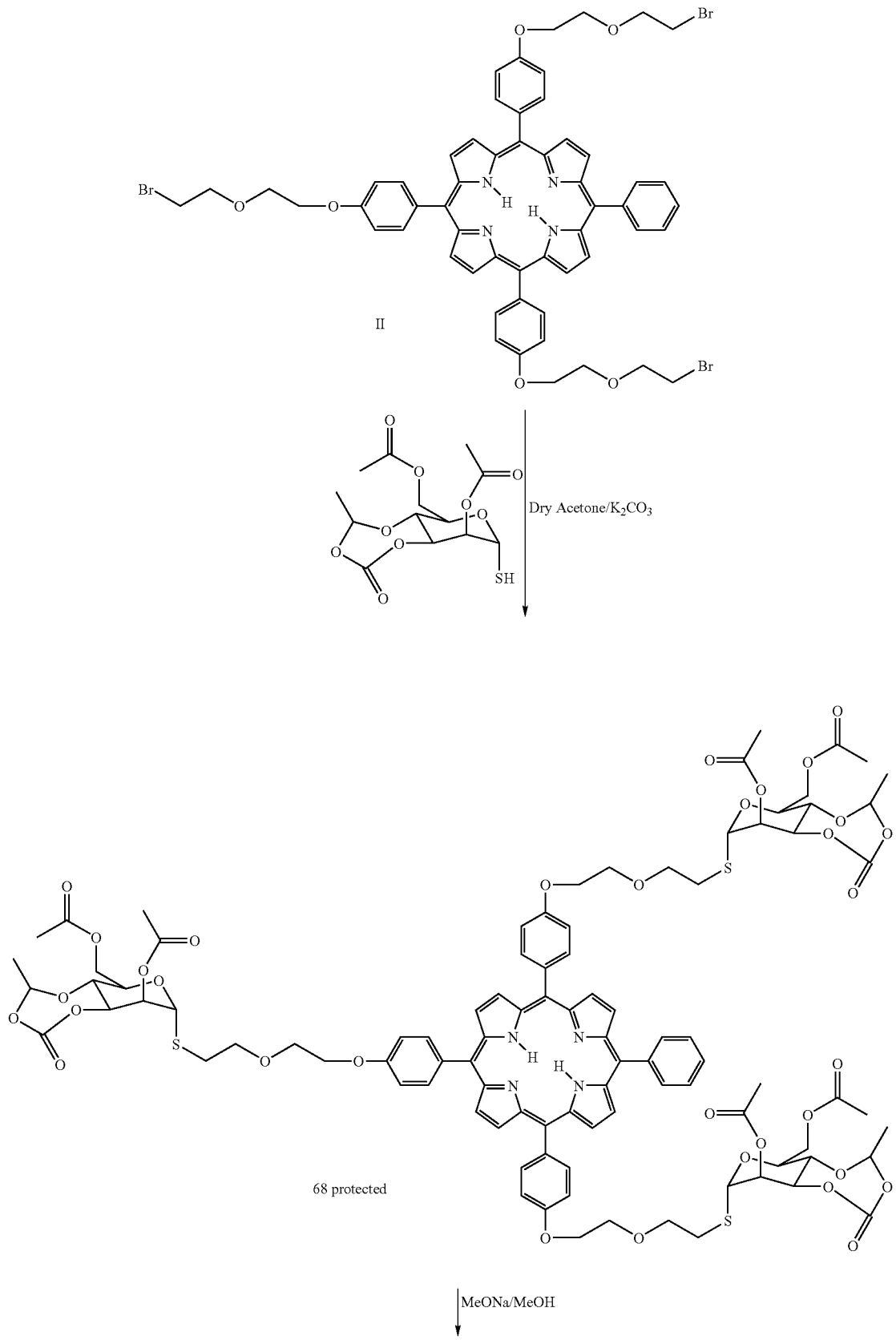

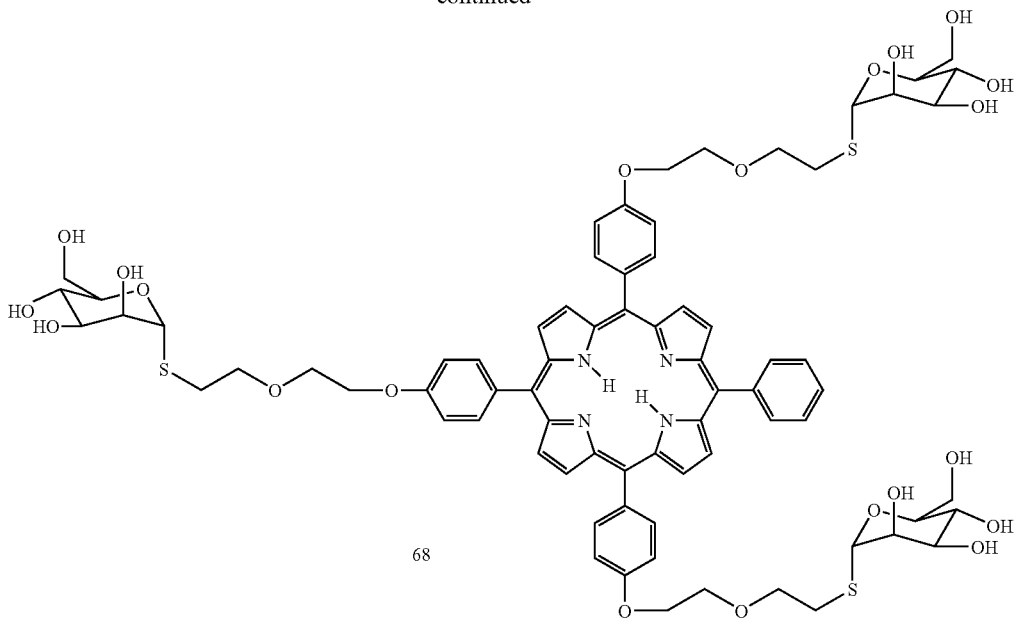

68

Compound II:

To a solution of 100 mg of 5,10,15-tri(para-hydroxyphenyl)-20-phenylporphyrin (I) ($1.10^{-4}$ mole) and 0.524 g of dibromo diethyleneglycol ($2.26 \, 10^{-3}$ mole) (Ref.: S. De, W. K. Aswal, P. S. Goyal, S. Bhattacharya *J. Phys. Chem. B* 102, 6152-6161, 1998) in DMF (20 mL) was added 0.621 g of $K_2CO_3$ ($4.5 \, 10^{-3}$ mole). The resulting mixture was stirred under argon overnight at room temperature and at 50° C. for an additional four hours. The reaction was then concentrated under vacuum, and the crude product mixture was taken up in methylene chloride, washed with water (3×), dried over sodium sulfate, filtered and concentrated. The title compound (87 mg, 51%; purple powder) was obtained pure after silica gel column chromatography (methylene chloride), and recrystallization from methylene chloride/heptane.

Protected Compound 68:

To a solution of 87 mg of compound II ($7.8 \, 10^{-5}$ mole) and 135 mg of α-D-thio-2,3,4,6-tetraacetyl-mannose ($0.37 \, 10^{-3}$ mole) in dry acetone (molecular sieve 4 Å) (25 mL) was added 100 mg of $K_2CO_3$ ($0.725 \, 10^{-3}$ mole). After stirring overnight at room temperature an additional 100 mg of α-D-thio-2,3,4,6-tetraacetyl-mannose was added. Stirring was continued until compound II could no longer be detected by silica gel thin layer chromatography [methylene chloride/ether (10/1, v/v)]. The reaction was then concentrated under vacuum, and the crude product mixture was taken up in methylene chloride, washed with water (3×), dried over sodium sulfate, filtered and concentrated. The crude mixture was partially separated by silica gel column chromatography [methylene chloride/ether (10/1 to 1/1, v/v)].

The more polar fraction was further purified by Sephadex LH120 exclusion column chromatography [methylene chloride/ethanol (1/1, v/v)]. The title compound was obtained as a red powder after crystallization from methylene chloride/cyclohexane (132 mg, 86%).

Compound 68:

75 mg of protected compound 68 was converted to compound 68 according to the general protocol described in reference 16. The title compound as a red powder was obtained in quantitative yield after crystalllization from methanol/1,2-dichloroethane containing a trace amount of pyridine.

The porphyrin compounds exhibit a very well characterized structure by physical measurements (UV visible spectroscopy, RMN), as follows for some of them.

Acetylated Compound 23

Yield: 58%.

Anal. Calcd for $C_{95}H_{102}N_4O_{30}S_3$ C, 60.82; H, 5.48; N, 2.99; S, 5.13. Found C, 59.30; H, 5.66; N, 2.46; S, 4.80.

UV-vis spectrum in $CHCl_3$: $\lambda_{max}$, nm (ε, L mmol$^{-1}$ cm$^{-1}$): 420 (410.9), 517(16.9),554 (11.7), 594 (7.2), 648.5 (7.4).

$^1$H NMR (CDCl$_3$) 8.88 (s, 6H, pyrrole), 8.84 (s 2H, pyrrole), 8.25 (d, 2H, $H_o$ phenyl, J=6.1 Hz), 8.13 (d, 6H, $H_o$, phenoxy, J=6 Hz), 7.77 (m, 3H, $H_m$ and $H_p$, phenyl), 7.30 (d, 6H, $H_m$, phenoxy, J=8 Hz), 5.30 (t, 3H, $H_3$ "ose", J=9.1 Hz), 5.16 (m, 6H, $H_3$, $H_4$ "ose"), 4.64 (d, 3H, $H_1$ "ose", J=8.2 Hz), 4.37-4.33-4.23 (m, 12H, $H_6$ "ose" and O—CH$_2$), 3.79 (d, 3H, $H_5$ "ose"), 3.08 (m, 6H, S—CH$_2$), 2.32 (q, 6H, CH$_2$), 2.18 (s, 6H, Acetyl), 2.14-2.13 (18H, Acetyl), 2.08 (12H, Acetyl), -2.74 (s, 2H, NH)

Compound 23

Yield: 100%.

Anal. Calcd for $C_{71}H_{78}N_4O_{18}S_3$ C, 62.17; H, 5.73; N, 4.08; S, 7.01. Found C, 38.70; H, 3.79; N, 3.71; S, 43.00.

WV-vis spectrum in MeOH/pyridine (24/1, v/v): $\lambda_{max}$, nm (relative Optical Density) 416 (1), 514 (0.066), 550 (0.054), 591 (0.044), 647 (0.042).

$^1$H NMR (Pyridine d$_5$) 9.5 (d, 2H, pyrrole, J=4.85 Hz), 9.18 (s, 4H, pyrrole), 9.1 (d, 2H, pyrrole, J=4.85 Hz), 8.37 (m, 2H, $H_o$ phenyl), 8.27 (dd, 6H, $H_o$ phenoxy, J=8.6 and 2.2 Hz), 7.79 (m, 3H, $H_m$ and $H_p$ phenyl), 7.39 (dd, 6H, $H_m$ phenoxy, J=8.6 and 2.2 Hz), 5.14 (d, 3H, $H_1$ "ose", J=9.6 Hz), 4.62 (m, 3H, $H_{6a}$ "ose"), 4.41 (m, 3H, $H_{6b}$ "ose"), 4.37 (3, 6H, OCH$_2$), 4.31 (m, 6H, $H_5$ and $H_3$ "ose"), 4.15 (m, 3H, $H_2$ "ose"), 4.05 (m, 3H, $H_4$ "ose"), 3.34 (m, 3H, S—CH$_{2a}$), 3.20 (m, 3H, S—CH$_{2b}$), 2.41 (dd, 6H, CH$_2$), -2.27 (s, 2H, NH).

¹³C NMR (Pyridine d₅) 159.5 (para-phenoxy), 142.7 ($C_1$ phenyl), 135.6 (ortho-phenoxy), 134.7 ($C_1$ phenoxy), 134.2 (ortho-phenyl), 131.8 (pyrrole), 127.4-126.4 (meta and para phenyl), 120.7 ($C_{meso}$), 112.9 (meta-phenoxy), 87.5 ($C_1$ sugar), 82.9 ($C_4$ "ose"), 80.3 ($C_3$ "ose"), 74.7 ($C_2$ "ose"), 71.6 ($C_5$ "ose"), 67.1 (O—CH₂), 63 ($C_6$ "ose"), 30.5 (—CH₂—), 27.3 (S—CH₂).

MALDI TOF spectrum for $C_{71}H_{78}N_4O_{18}S_3$: Calc. 1370.5; found: 1371.45 M+1

Acetylated Compound 24
Yield: 51%.
Anal. Calcd for $C_{95}H_{102}N_4O_{30}S_3$ C, 60.82; H, 5.48; N, 2.99; S, 5.13. Found C, 59.64; H, 5.81; N, 2.34; S, 5.31.
UV-vis spectrum in CHCl₃: $\lambda_{max}$, nm ($\epsilon$, L mmol⁻¹ cm⁻¹): 418.5 (409.6), 515 (17.3), 550 (12.9), 590 (7.2), 646.5 (7.1).

¹H NMR (CDCl₃) 8.90-8.89-8.86-8.85 (8H, pyrrole), 8.24 (d, 2H₀, phenyl, J=7.5 Hz), 8.15 (d, 6H₀, phenoxy, J=8.4 Hz), 7.79 (d, 3 H_m and H_p, phenyl, J=6.5 Hz), 7.30 (d, 6 H_m, phenoxy, J=7 Hz), 5.40 (m, 9H, "ose"), 4.53 (m, 3H, "ose"), 4.38 (m, 9H, "ose" and CH₂—O), 4.20 (m, 6H, "ose"), 3.04 (m, 6H, CH₂), 2.35 (Q, 6H, CH₂—S), 2.23 (s, 6H, Acetyl), 2.19 (s, 9H, Acetyl), 2.14 (s, 3H, Acetyl), 2.11 (s, 6H, Acetyl), 2.09 (s, 3H, Acetyl), 2.05 (s, 6H, Acetyl), 2.04 (s, 3H, Acetyl), -2.73 (s, 2H, NH).

Compound 24
Yield: 90%.
Anal. Calcd for $C_{71}H_{78}N_4O_{18}S_3$ C, 62.17; H, 5.73; N, 4.08; S, 7.01. Found C, 38.59; H, 4.10; N, 2.19; S, 4.31.
UV-vis spectrum in MeOH/pyridine 24/1, v/v, $\lambda_{max}$, nm ($\epsilon$, L mmol⁻¹ cm⁻¹): 416 (214.9), 514.5 (11), 550.5 (8.3), 589 (5.7), 647.5 (5.6).

¹H NMR (Pyridine d₅) 9.17-9.07 (m, 8H, pyrrole), 8.39 (m, 2H, H₀ phenyl), 8.29 (d, 6H, H₀ phenoxy, J=8.6 Hz), 7.86 (m, 3H, H_m and H_p phenyl), 7.45 (d, 6H, H_m phenoxy, J=8.6 Hz), 5.43 (d, 3H, H₁ "ose", J=1.5 Hz), 5.37 (dd, 3H, H₂ "ose"), 4.75 (m, 6H, H₃ and H₄ "ose"), 4.61 (dd, 3H, H_{6a} "ose"), 4.43 (t broad, 3H, O—CH₂), 4.31 (dd, 3H, H_{6b} "ose"), 4.30 (m, 3H, H₅ "ose"), 3.72 (m, 3H, S—CH_{2a}), 3.39 (m, 3H, S—CH_{2b}), 2.64 (m, 6H, —CH₂—S), -2.31 (s, 2H, NH).

³C NMR (Pyridine d₅) 159.5 (para-phenoxy), 143 ($C_1$ phenyl), 136 (ortho-phenyl), 135.2 ($C_1$ phenoxy), 131 (CH pyrrole), 128.5 (meta or para phenyl), 127.6 (para or meta phenyl), 121 (C meso), 113.8 (meta phenoxy), 96.6 ($C_1$ "ose"), 82 ($C_5$ "ose"), 73.1 ($C_3$ "ose"), 68 ($C_4$ "ose"), 68.4 ($C_2$ "ose"), 67.4 (O—CH₂), 63 ($C_6$ "ose"), 47.3 S—CH₂), 23.1 (CH₂).

MALDI TOF spectrum for $C_{71}H_{78}N_4O_{18}S_3$: Calc. 1370, 45; found: 1371.43 M+1

Compound 25 (Glycosylation, Protected Porphyrin):
Anal. Calcd for $C_{100}H_{86}N_4O_{36}F_{16}S_4$ C, 51,07; H, 3,69; N, 2,38; S, 5,45%, found C, 51,40; H, 4,32; N, 1,98; S, 5,43%
UV visible $CH_2Cl_2$ $\lambda_{max}$, nm ($\epsilon$, L mmol⁻¹ cm⁻¹): 414,5 (340.5), 507 (24.4), 538 (shoulder), 585 (4.9), 649 (shoulder).

¹H NMR (CDCl₃) 9.03 (s, 8H, pyrrole), 5.39 (t, 4 HC₃, "ose", J=8.9 Hz), 5.25 (m, 8H, HC₂ and HC₄ "ose"), 5.18 (d, 4H, HC₁ "ose", J=8.9 Hz), 4.33 (d, 4H, HC₆ "ose"), 4.32 (m, 4H, HC₆ "ose"), 3.91 (m, 4H, HC₅ "ose"), 2.23 (s, 12H, Acetyl), 2.10 (s, 12H, Acetyl), 2.09 (s, 12H, Acetyl), 2.08 (s, 12H, Acetyl), -2.86 (s, 2H, NH).

¹³C NMR (CDCl₃) 170.7, 170.22, 169.53, 169.45 (C=O acetyl), 147.12 (dd, meta or ortho phenyl, $J_{C-F}$=256 Hz, $J_{C-C-F}$=15 Hz), 146.34 (dd, meta or ortho phenyl, $J_{C-F}$=254 Hz, $J_{C-C-F}$=15 Hz), 131.6 (CH pyrrole), 122.12 (t, meso C phenyl, $J_{C-C-F}$=19 Hz), 111.93 (t, para-phenyl, $J_{C-C-F}$=20.5 Hz), 104.34 (meso C), 84.5 ($C_1$ "ose"), 76.49 ($C_5$ "ose"), 73.98 ($C_3$ "ose"), 70.67 ($C_2$ "ose"), 68.14 ($C_4$ "ose"), 61.87 ($C_6$ "ose"), 20.71, 20.66 (CH₃ acetyl).

Compound 25 (Deacetylation):
Yield 95%
Anal. Calcd for $C_{68}H_{54}F_{16}N_4O_{20}S_4$ 3H₂O C, 48.93; H, 3.62; N, 3.36; S, 7.64 Found C, 48.75; H, 3.34; N, 3.34.
UV-vis spectrum in Methanol: $\lambda_{max}$, nm ($\epsilon$, L mmol⁻¹ cm⁻¹): 409.5 (257.5), 504 (18), 535 (4.5), 581.5 (7), 639 (2.8)

¹H NMR (Pyridine d₅) 9.44 (s, 8H, pyrrole), 8.31 (d, 4H, HOC₂ "ose", J=4.85 Hz), 7.75 (d, 4H, HOC₃ "ose", J=2.70 Hz), 7.43 (d, 4H, HOC₄ "ose", J=4.75 Hz), 6.81 (t, 4H, HOC₆ "ose", J=5.65 Hz), 5.92 (d, 4H, HCl "ose", J=8.6 Hz), 4.72 (dd, 4H, HC₆ "ose", J=8.55 and 4.7 Hz), 4.4 (m, 8H, HC₂ and HC₃ "ose"), 4.37 (m, 4H, HC₆ "ose"), 4.30 (m, 4H, HC₄ "ose"), 4.19 (m, 4H, HC₅ "ose"), -3.05 (s, 2H, NH).

¹³C NMR (Pyridine d₅) 148 (dd, ortho or meta phenyl, $J_{CF}$=250 Hz, $J_{CCF}$=15 Hz), 146.78 (dd meta or ortho phenyl, $J_{CF}$=250 Hz, $J_{CCF}$=15 Hz), 132.3 (CH pyrrole), 120.72 (C meso phenyl), 115.26 (para-phenyl), 105.04 (meso C), 86.57 ($C_1$ "ose"), 83.65 ($C_5$ "ose"), 80.39 ($C_3$ "ose"), 76.38 ($C_2$ "ose"), 71.96 ($C_4$ "ose"), 63.05 ($C_6$ "ose").

MALDI-TOF spectrum for $C_{68}H_{54}F_{16}N_4O_{20}S_4$: Calc. 1678.11; found: 1679.16 M+1

Acetylated Compound 26
Yield: 48%.
Anal. Calcd for $C_{86}H_{67}N_4O_{27}F_{17}S_3$ C, 51.45; H, 3.36; N, 2.79; S, 4.79. Found C, 51.16; H, 3.98; N, 2.16; S, 4.86.
WV-vis spectrum in CHCl₃: $\lambda_{max}$, nm ($\epsilon$, L mmol⁻¹ cm⁻¹): 413.5 (294.1), 507(20.9), 538 (shoulder), 583.5 (8.6), 649 (4.7).

¹H NMR (CDCl₃) 9.0 (s, 2H, pyrrole), 8.93 (s, 6H, pyrrole), 6.25 (d, 3H, H₁ "ose", J=5.5 Hz), 5.64 (t, 3H, H₃ "ose", J=8.3 Hz), 5.40-5.09 (m, 6H, H₂ and H₄ "ose"), 4.82 (m, 3H, H₅ "ose"), 4.42-4.23 (m, 6H, H₆ "ose"), 2.26, 2.22, 2.13, 2.11, 2.08, 2.06, 2.02, 1.99 (s, 36H, Acetyl), -2.91 (s, 2H, NH).

¹³C NMR (CDCl₃) 169.64 (C=O, acetyl), 169.17 (C=O, acetyl), 168.47 (C=O, acetyl), 168.39 (C=O, acetyl), 146.14 (dd, C ortho or meta phenyl, $J_{C-F}$=250 Hz, $J_{C-C-F}$=15 Hz), 145.39 (dd, C meta or ortho phenyl, $J_{C-F}$=250 Hz, $J_{C-F}$=15 Hz), 130.5 CH pyrrole), 121.1 (t, C phenyl, $J_{C-C-F}$=19 Hz), 114.64 (t, C $C_6F_5$, $J_{C-C-}$F=20 Hz), 110.89 (t, para phenyl, $J_{C-CF}$=20 Hz), 103.28 (meso C $C_6F_4$), 102.61 (meso C $C_6F_5$), 102.61 (meso C $C_6F_5$), 83.43 ($C_1$ "ose"), 75.41 ($C_5$ "ose"), 72.93 ($C_3$ "ose"), 69.61 ($C_2$ "ose"), 67.08 ($C_4$ "ose"), 60.81 ($C_6$ "ose"), 19.65 (CH₃ acetyl), 19.60 (CH₃ acetyl).

Compound 26
Yield: 95%
Anal. Calcd for $C_{62}H_{43}N_4F_{17}O_{15}S_3$ C, 49.54; H, 2.88; N, 3.73; S, 6.40. Found C, 45.99; H, 3.17; N, 4.25; S, 5.23.
WV-vis spectrum in Methanol: $\lambda_{max}$ nm ($\epsilon$, L mmol¹ cm⁻¹): 409 (283.7), 503.5 (19.9), 536 (4.3), 581 (7.2), 647 (2.5)

¹H NMR (Pyridine d₅) 9.6 and 9.48 (m, 8H, pyrrole), 8.33 (t, 3H OH "ose"), 7.77 (t, 3H, OH "ose"), 7.45 (t, 3H, OH "ose"), 6.81 (t, 3H, OH "ose"), 5.94 (C, 3H, HC₁ "ose", J=7.7 Hz), 4.72 (dd, 3H, HC₆ "ose"), 4.4 (m, 9H, C₂, C₃ and C₄ "ose"), 4.35 (dd, 3H, HC₆ "ose"), 4.2 (m, 3H, HC₅ "ose"), -3.05 (s, 2H, NH).

¹³C NMR (Pyridine d₅) 147.9 (d, $C_2$ or $C_3$ phenyl, $J_{CF}$=250 Hz, $J_{CCF}$=15 Hz), 146.78 (d, $C_3$ or $C_2$ phenyl, $J_{CF}$=250 Hz, $J_{CCF}$=15 Hz), 132 (C pyrrole), 120.61 (t, C, phenyl, $J_{CCF}$=19 Hz), 115.37 (t, $C_4$ phenyl, $J_{CCF}$=21 Hz), 105.22 (meso C), 86.59 ($C_1$ "ose"), 83.65 ($C_5$ "ose"), 80.4 ($C_{2/3}$ "ose"), 76.39 ($C_{3/2}$ "ose"), 71.97 ($C_4$ "ose"), 63.05 ($C_6$ "ose"), MALDI TOF spectrum for $C_{62}H_{43}N_4F_{17}O_{15}S_3$: Calc. 1502.16; found: 1503.15 M+1

Acetylated Compound 29

Yield: 58%.

Anal. Calcd for $C_{100}H_{86}N_4O_{36}F_{16}S_4$ C, 51.07; H, 3.69; N, 2.38; S, 5.45. Found C, 51.40; H, 4.27; N, 1.84; S, 4.86. WV-vis spectrum in $CHCl_3$: $\lambda_{max}$, nm ($\epsilon$, L mmol$^{-1}$ cm$^{-1}$): 412.5(327.4), 505 (23.6), 537 (shoulder), 582.5 (10), 640 (shoulder).

$^1$H NMR (CDCl$_3$) 8.87 (8H, pyrrole), 5.68 (m, 4H, "ose"), 5.53-5.23 (m, 12H, "ose"), 4.35-4.10 (m, 8H, "ose"), 3.55 (m, 4H, "ose"), 2.20, 2.09, 2.04, 2.00, 1.99, 1.94 (48H, Acetyl), −2.97 (s, 2H, NH).

Compound 29

Yield: 90%.

Anal. Calcd for $C_{68}H_{54}F_{16}N_4O_{20}S_4$ 3H$_2$O C, 46.63; H, 3.57; N, 3.20; S, 7.32 Found C, 46.36; H, 3.47; N, 3.58; S, 5.95. UV-vis spectrum in Methanol: $\lambda_{max}$, nm ($\epsilon$, L mmol$^{-1}$ cm$^{-1}$): 408.5 (240.9), 503 (20.2), 534 (shoulder), 580.5 (9.9), 640 (shoulder) $^1$H NMR (Pyridine d$_5$) 9.48 (broad, 8H, pyrrole), 7.73 (broad, 4H, OH "ose"), 7.4 (broad, 4H, OH "ose"), 7.29 (broad, 4H, OH "ose"), 6.95 (broad, 4H, OH "ose"), 6.83 (s, 4H, HC$_1$ "ose"), 4.95 (m, 8H, HC$_2$ and HC$_3$ "ose"), 4.90 (m, 4H, HC$_5$ "ose"), 4.75 (m, 4H, HC$_4$ "ose"), 4.75 (m, 4H, HC$_6$ "ose"), 4.41 (dd, 4H, HC$_6$ "ose", J=12.2 and 7.9 Hz), −3.1 (broad, 2H, NH).

$^{13}$C NMR (Pyridine d$_5$) 148 (dd C$_3$ phenyl, J$_{CF}$=250 and 18 Hz), 146.86 (dd, C$_2$ phenyl, J$_{CF}$=248 and 15 Hz), 133 (CH pyrrole), 121.27 (C$_1$ phenyl, J$_{CCF}$=19.5 Hz), 114.32 (C$_4$ phenyl, J$_{CCF}$=20 Hz), 104.98 (meso C), 87.74 (C$_1$ sugar), 78.12 (C$_5$ "ose"), 73.4 (C$_{2/3}$ "ose"), 72.86 (C$_{3/2}$ "ose"), 69.29 (C$_{14}$ "ose"), 62.76 (C$_6$ "ose").

MALDI TOF spectrum for $C_{68}H_{54}F_{16}N_4O_2OS_4$: Calc. 1678.11; found: 1679.11 M+1, 1485.15 (M+2H-Mann-S—), 1291.17 15 (M+2H-2Mann-S—) 1077.11 (M+2H-3Mann-S—), 1070.13 (M+2H-3Mann-S—, -1F), 861.16 (M+2H-4Mann-S—, -2F).

Acetylated Compound 31

Yield: 15%.

Anal. Calcd for $C_{72}H_{48}N_4O_{18}F_{18}S_2$ C, 51.99; H, 2.91; F, 20.56; N, 3.37; S, 3.86.

Found C, 51.34; H, 2.85; N, 3.26; S, 3.75. WV-vis spectrum in CH$_2$Cl$_2$: $\lambda_{max}$, nm ($\epsilon$, L mmol$^{-1}$cm$^{-1}$): 413 (240.4), 507 (14), 537 (shoulder), 584 (6.2), 655 (shoulder).

$^1$H NMR (CDCl$_3$) 8.87-8.84 (m 8H, pyrrole), 5.82 (2H, "ose"), 5.67 (m, 2H, "ose"), 5.46 (m, 4H, "ose"), 4.68 (m, 2H, H$_5$ "ose"), 4.34 (dd, 2H, H$_{6a}$, "ose", J=5.4 and 12.4 Hz), 4.20 (dd, 2H, H$_{6b}$ "ose", J=1.7 and 12.4 Hz), 2.18 (s, 6H Acetyl), 2.07 (s, 6H Acetyl), 2.02 (s, 6H Acetyl), 1.99 (s, 6H Acetyl), −2.98 (s, 2H, NH).

Compound 31

Yield: 90%.

Anal. Calcd for $C_{56}H_{32}N_4O_{10}F_{18}S_4$ C, 50.69; H, 2.43; N, 4.22; S, 4.83. Found C, 47.08; H, 4.91; N, 2.11; S, 2.56. UV-vis spectrum in methanol: $\lambda_{max}$, nm ($\epsilon$, L mmol$^{-1}$cm$^{-1}$): 408 (152), 503 (8.4), 537 (shoulder), 581 (3.6), 640 (shoulder).

MALDI TOF spectrum for $C_{56}H_{32}N_4O_{10}F_{18}S_4$: Calc. 1326.13; found: 1327.14 M+1

Compound 54 (Protected):

Yield 89%

Anal. Calcd for $C_{100}H_{104}N_4O_{40}$; C 58,94; H 3,54; N 2,76% found C 58,86; H 5,40; N 2,73% UV visible CH$_2$C$_2$ $\lambda_{max}$, nm ($\epsilon$, L mmol$^{-1}$cm$^{-1}$): 412 (324,3), 505 (24), 537 (shoulder), 581,5 (10,1), 642 (shoulder)

$^1$H NMR (CDCl$_3$): 8.61 (d, 2H, pyrrole), 8.45 (d, broad, 2H, pyrrole), 8.24 (d, 2H, pyrrole, J=3 Hz), 7.80 (broad, 4H, para-phenyl), 7.63 (broad, 8H, ortho-phenyl), 7.34 (broad, 4H, meta-phenyl), 5.34 (m, 12H, HC$_1$, HC$_2$, HC$_3$ «ose»), 5.17 (m, 4H, HC$_4$ «ose»), 4.19 (m, 8H, HC$_6$ «ose»), 4.06 (m, 4H, HC$_2$, HC$_3$ pyrrole), 3.81 (m, 4H, HC$_5$ «ose»), 2.09 (s), 2.07 (s), 2.03 (s) (48H, Acetyl), −1.54 (s, 2H, NH).

MALDI TOF spectrum for $C_{100}H_{104}N_4O_{40}$: Calc. 2000, 62; found: 2001,76 M+1

Compound 54 (Deacetylation):

Yield: 94%

Anal. Calcd for $C_{68}H_{72}N_4O_{24}$ C 61.44; H 5.46; N 4.21%, found C 48.03; H 4.36; N 2.89% UV visible MeOH $\lambda_{max}$, nm ($\epsilon$, L mmol$^{-1}$cm$^{-1}$): 415 (183.9), 515.5 (14.4), 542.5 (10.1), 596 (6.7); 650 (27.7)

$^1$H NMR (pyridine d$_5$) 8.73 (m, 2H, pyrrole), 8.34 (m, 2H, pyrrole), 8.22 (m, 2H, pyrrole), 8.03-7.55 (m, 8H, phenyl), 7.50-7.10 (m, 8H, phenyl), 6.65 (broad, 4H, OH), 5.92 (broad, 4H, OH), 4.40 (m, 22H, «ose»), 4.08 (m, 8H, «ose»and pyrrole), −1.36 (s, 2H, NH).

MALDI TOF spectrum for $C_{68}H_{72}N_4O_{24}$: Calc. 1327.45; found: 1328.47 M+1

Compound II $^1$H NMR (CDCl$_3$), δ (ppm): 8.85 (m, 8H, pyrrole), 8.21 (m, 2H, ortho-phenyl), 8.10 (d, 6H, ortho phenoxy, J=8.4 Hz), 7.75 (m, 3H, meta and para phenyl), 7.26 (d, 6H, meta phenoxy, J=8.4 Hz), 4.33 (t, 6H, O—CH$_2$), 4.03 (t, 6H, O—CH$_2$), 4.0 (t, 6H, O—CH$_2$, J=6.3 Hz), 3.59 (t, 6H, Br—CH$_2$, J=6.3 Hz), −2.75 (s, 2H, NH).

$^{13}$C NMR (CDCl$_3$), δ (ppm): (ppm): 158.6 (para phenoxy), 142, 135 (C-phenyl-meso-C), 135.5 (ortho phenoxy), 133.9 (para phenyl), 130.8 (C-pyrrole), 127 (meta phenyl), 119.5 (meso-C), 112.5 (meta phenoxy), 71.4 (O—CH$_2$—CH$_2$Br), 69.7 (O—CH$_2$—CH$_2$O), 67.5 (O—CH$_2$—CH$_2$O), 30.1 (O—CH$_2$—CH$_2$Br), Compound 55 (Protected Porphyrin)

Yield: 72%

Anal. Calcd for $C_{68}H_{72}N_4O_{24}$, H$_2$O: C, 60.62; H, 5.54; N, 4.16; Found C, 60.32; H, 5.45; N, 4.20. UV-visible spectrum in MeOH $\lambda_{max}$, ($\epsilon$ L.mmole$^{-1}$ cm$^{-1}$): 415 (183.9), 515.5 (14.4), 542.5 (10.1), 596 (6.7), 650 (27.7).

$^1$H NMR (pyridine d$_5$) 8.73 (m, 2H, pyrrole), 8.34 (m, 2H, pyrrole), 8.22 (m, 2H, pyrrole), 8.03-7.55 (m, 8H, phenyl), 7.50-7.10 (m, 8H, phenyl), 6.65 (broad, 4H, OH), 5.92 (broad, 4H, OH), 4.40 (m, 22H, «ose»), 4.08 (m, 8H, «ose»and pyrrole), −1.36 (s, 2H, NH).

MALDI TOF spectrum for $C_{68}H_{72}N_4O_{24}$: Calc. 1328.45; found: 1329.70 M+1.

Compound 55 (Deacetylation)

5,10,15-Tri(3-O-β-D-glucosylphenyl)-2,3-chlorin and 5,10,15-tri(3-O-β-D-glucosylphenyl)-7,8-chlorin, Yield of isomers 80%.

Anal. Calcd for $C_{62}H_{62}N_4O_{18}H_2O$: C, 63.69; H, 5.52; N, 4.79; Found C, 63.29; H, 5.38; N 4.90. UV-vis spectrum in MeOH: $\lambda_{max}$, nm ($\epsilon$ L mmol$^{-1}$ cm$^{-1}$): 414.5 (237.9), 515 (17.3), 542 (12), 595.5 (8), 649.5 (32.8).

MALDI TOF spectrum for $C_{62}H_{62}N_4O_{18}$: Calc. 1150.40; found: 1151.52. M+1

Compound 67 (Protected Porphyrin)

Yield 23%

Anal. Calcd for $C_{98}H_{108}N_4O_{36}$ 2H$_2$O: C, 60.24; H, 5.78; N, 2.87; Found C, 60.25; H, 5.92; N 2.66. WV-vis spectrum in CH$_2$Cl$_2$, TEA: $\lambda_{max}$, nm ($\epsilon$ L mmol$^{-1}$ cm$^{-1}$): 419.5 (429.5), 516 (16.8), 553 (10.5), 592.5 (5.5), 647.5 (5.3).

$^1$H NMR, CDCl$_3$, δ (ppm): 8.86 (s, 4H, pyrrole), 8.86 (d, 2H, pyrrole, J=4.8 Hz), 8.63 (d, 2H, pyrrole, J=5.8 Hz), 8.22 (dd, 2H, ortho-phenyl, J=7.6 and 1.6 Hz), 8.10 (d, 6H, ortho-phenoxy), 7.75 (m, 3H, meta and para-phenyl), 7.31 (d, 6H, meta-phenoxy), 5.47 (dd, J=3.4 Hz and 10.1 Hz), 5.35 (m) (3H, HC$_2$, HC$_3$ and HC$_4$ "ose"), 4.99 (s, 3H, HC$_1$ "ose"), 4.42 (m, 3H, HC$_5$ "ose"), 4.42 (m, 6H, CH$_2$—O-phenyl), 4.36 (dd, 3H, HC$_{6a}$ "ose", J=4.8 and 12 Hz), 4.16 (m, HC$_{6b}$ "ose"), 4.06 (m, 6H, O—CH$_2$ CH$_2$—O-phenyl), 3.95 (m, 6H, O—CH$_2$), 3.88 (m, 6H, O—CH$_2$CH$_2$—O), 3.60 (m, 6H, CH$_2$), 2.18 (s, 9H, acetyl), 2.14 (s, 9H, acetyl), 2.04 (s, 9H, acetyl), 2.0 (s, 9H, acetyl), −2.76 (s, 2H, NH).

$^{13}$C NMR (CDCl$_3$), δ (ppm):170.7 (CO acetyl), 170.1 (CO acetyl), 170 (CO acetyl), 169.8 (CO acetyl), 158.7 (C$_4$ phenoxy), 142.3 (C$_1$ phenyl), 135.7 (C$_2$ phenoxy), 134.9 (C$_1$ phenoxy), 134.65 (C$_2$ phenyl), 131 (broad, CH pyrrole), 127.8 (C$_4$ phenyl), 126.8 (C$_3$ phenyl), 119.9-119.8 (meso-C), 112.9 (C$_3$ phenoxy), 97.95 (C$_1$ "ose"), 70.4 (C$_2$ "ose"), 70.1 (CH$_2$CH$_2$—O-phenyl), 69.7 (C$_4$ "ose"), 69.2 (C$_5$ "ose"), 68.6 (CH$_2$), 67.8 (CH$_2$), 67.6 (CH$_2$—O-phenyl), (C$_3$ "ose"), 62.5 (C$_6$ "ose"), 22.7 (CH$_3$, acetyl), 20.85 (CH$_3$, acetyl), 20.78 (CH$_3$, acetyl), 20.75 (CH$_3$, acetyl).

Compound 67 (Deacetylation)
Yield 90%
Anal. Calcd for C$_{74}$H$_{84}$N$_4$O$_{24}$ 4H$_2$O: C, 59.83; H, 6.24; N, 3.77; Found C, 59.25; H, 5.93; N 3.58. UV-vis spectrum in MeOH/pyridine 24/1, v/v: λ$_{max}$, nm (ε L mmol$^{-1}$ cm$^{-1}$): 417.5 (359.5), 515.5 (15.3), 551.5 (10.5), 592 (6.3), 648 (6).
MALDI TOF spectrum for C$_{74}$H$_{84}$N$_4$O$_{24}$: Calc. 1412.55; found: 1413.65 M+1.

Compound 68 (Protected)
Yield 86%
UV visible CH$_2$Cl$_2$ λ$_{max}$, nm, (ε L mmol$^{-1}$ cm$^{-1}$): 421 (380), 517.5 (14.4), 552 (9.2), 593 (4.6), 649.5 (4.6)
$^1$H NMR, CDCl$_3$, δ (ppm): 8.84, (m, 8H, pyrrole), 8.22 (dd, 2H, ortho-phenyl, J=7 and 2 Hz), 8.11 (d, 6H, ortho-phenoxy, J=8.6 Hz), 7.75 (m, 3H, meta and para-phenyl), 7.29 (d, 6H meta-phenoxy, J=8.6 Hz), 5.47 (d, 3H, H$_1$ "ose", J=1.3 Hz), 5.44 (dd, 3H, H$_2$ "ose", J=1.3 Hz), 4.47 (m, 3H, H$_5$ "ose"), 4.40 (m, 6 H, CH$_2$—O-phenyl), 4.37 (dd, 3H, H$_{6a}$ "ose", J=12.4 and 5.2 Hz), 4.16 (dd, 3H, H$_{6b}$ "ose", J=12.2 and 2.1 Hz), 4.02 (m, 6H CH$_2$—CH$_2$—O-phenyl), 3.90 (m, 6H, CH$_2$—CH$_2$—S), 3.03 (m, 3H, CH$_2$—S), 2.89 (m, 3H, CH$_2$—S), 2.18, 2.14, 2.05, 2.00 (s, 4×9H, acetyl), −2.76 (s, 2H, NH).
$^{13}$C NMR, CDCl$_3$, δ (ppm): 170.6, 170, 169.9, 169.7, (C=O, Acetyl), 158.5 (C$_4$ phenoxy), 142.2 (C$_1$ phenyl), 135.6 (C$_2$ phenoxy), 134.8 (C$_1$ phenoxy), 134.5 (C$_2$-phenyl), 131 (C β-pyr), 127.6 (C$_4$ phenyl), 126.6 (C$_3$ phenyl), 119.8, 119.7, 119.7 (C$_3$ phenoxy), 82.9 (C$_1$ "ose"), 71.0 (C$_2$ "ose"), 70.8 (CH$_2$—CH$_2$—S), 69.7 (CH$_2$—CH$_2$—O-Ph), 69.4 (C$_4$-"ose"), 69.1 (C$_5$ "ose"), 67.6 (CH$_2$—O-phenyl), 66.3 (C$_3$ "ose"), 62.4 (C$_6$ "ose"), 30.7 (CH$_2$—S), 26.9 (CH$_2$), 20.9, 20.8, 20.7, 20.6 (CH$_3$, acetyl)

Compound 68 (Deacetylation):
Yield 100%
UV visible Methanol/Pyridine 24/1 λ$_{max}$, nm, (ε L mmol$^{-1}$ cm$^{-1}$): 417 (275.7), 515 (11.6), 552.5 (7.7), 592.4 (4), 647.5 (3.9).
$^1$H NMR, Pyridine d$_5$, δ (ppm): 9.17 (s, 4H, pyrrole), 9.13 (d, 2H, pyrrole, J=4.8 Hz), 9.06 (d, 2H, pyrrole, J=4.8 Hz), 8.38, (dd, 2H, ortho-phenyl, J=7.1 and 2.2 Hz), 8.26 (dd, 6H, meta-phenoxy, J=8.7 and 2.3 Hz), 7.80 (m, 3H, meta and para-phenyl), 7.44 (dd, 6H, meta-phenyl, J=8.7 and 2.3 Hz), 6.09 (d, 3H, H1 "ose", J=0.9 Hz) 4.84-4.59 (m, 12H, H$_2$, H$_3$, H$_4$, H$_5$ "ose"), 4.65 (m, 3H, H$_{6a}$ "ose"), 4.46 (m, 3H, 3H, H$_{6b}$ "ose"), 4.40 (m, 6H, CH$_2$—O-Ph), 3.99 (m 6H CH$_2$—CH$_2$—O-Ph), 3.94 (m, 3H, CH$_2$—CH$_2$—S), 3.26 (m, 3H, CH$_2$—S), 3.04 (m, 3H, CH$_2$—S), −2.28 (s, 2H, NH).
$^{13}$C NMR, Pyridine d$_5$, δ (ppm): 159.3 (C-para-phenoxy), 142.6 (C) phenyl, 136 (C$_2$ phenoxy), 135 (C1 phenyl), 134.7 (C$_2$ phenyl), 133 (broad, C pyrrole), 128 (C$_4$ phenyl), 127.3 (C$_3$ phenyl), 120.7-120.6-120.4 (C$_7$ meso), 113.5 (C$_3$ phenoxy), 86.8 (C$_1$ "ose"), 75.9 (C$_4$ "ose"), 73.6-73.5 (C$_2$ and C$_3$ "ose"), 71.3 (CH$_2$—CH$_2$—S), 69.6-69.4 (CH$_2$—CH$_2$—O-phenyl and C$_5$ "ose"), 68.0 (CH$_2$—O-phenyl), 63 (C$_6$ "ose"), 30.8 (CH$_2$—S).
MALDI TOF spectrum for C$_{74}$H$_{84}$N$_4$O$_{21}$S$_3$ calc. 1460.48; found: 1461.40 for M+1

Compound 77-78:
TPC(m-OH)$_3$ 5, 10, 15-tri(meta-hydroxyphenyl)-20-phenyl)-2,3-chlorin and 5,10,15-tri(3-hydroxyphenyl)-7,8-chlorin, mixture of 2 isomers
UW-vis spectrum Acetone: λ$_{max}$, nm (ε L mmol$^{-1}$ cm$^{-1}$): 416 (121), 516 (10.2), 542 (7), 597 (4.3), 650.5 (24.4)
$^1$H NMR (Acetone d$_6$), δ (ppm):
5,10,15-tri(meta-hydroxyphenyl)-20-phenyl)-2,3-chlorin: 8.65 (s, 3H, OH), [8.70 (d, H pyrrole, J=4.9 Hz), 8.68 (d, H pyrrole, J=5.2 Hz), 8.59 (d, H pyrrole, J=4.9 Hz), 8.31 (m, pyrrole), 8.19 (d, H pyrrole, J=4.9 Hz), 6H], 8.47 (s, 2H, HC$_{12}$ and HC$_{13}$ pyrrole), 7.89-7.15 (M, 17H, phenyl and phenoxy), 4.23 (m, 2H, CH$_2$ pyrrole), 4.17 (m, 2H, CH$_2$ pyrrole), −1.44 (s, 2H, NH).
5,10,15-tri(meta-hydroxyphenyl)-20-phenyl)-7,8-chlorin: 8.65 (s, 3H, OH), [8.70 (d, H pyrrole, J=4.9 Hz), 8.68 (d, H pyrrole, J=5.2 Hz), 8.59 (d, H pyrrole, J=4.9 Hz), 8.31 (m, pyrrole), 8.19 (d, H pyrrole, J=4.9 Hz), 6H], 8.46 (d, 1H, HC$_{17}$ or HC$_{18}$ pyrrole, J=4.4 Hz), 8.36 (d, 1H, HC$_{18}$ or HC$_{17}$ pyrrole, J=4.4 Hz), 7.89-7.15 (M, 17H, phenyl and phenoxy), 4.23 (s, 4H, CH$_2$ pyrrole), −1.44 (s, 2H, NH).
$^{13}$C NMR (Acetone d$_6$), δ (ppm):
5,10,15-tri(meta-hydroxyphenyl)-20-phenyl)-2,3-chlorin: 168.58 (C$_1$ pyrrole), 168.50 (C$_4$ pyrrole), 153.13 (broad, C$_{11-14}$ pyrrole), 141.32 (C$_6$ pyrrole), 141.24 (C$_{19}$ pyrrole), 135.77 (C$_9$ pyrrole), 135.67 (C$_{16}$ pyrrole), 132.51 (CH pyrrole), 113.27 (meso C), 128.94, 128.4, 124.34, 124.08 (C phenyl and phenoxy), 36.34 (C$_3$ pyrrole), 36.20 (C$_2$ pyrrole).
5,10,15-tri(meta-hydroxyphenyl)-20-phenyl)-7,8-chlorin: 168.50 (C$_6$ and C$_9$ pyrrole), 153.13 (broad, C$_{16-19}$ pyrrole), 141.32 (C$_{11}$ and C$_4$ pyrrole), 135.77 (C$_{14}$ and C$_1$ pyrrole), 132.51 (CH pyrrole), 113.27 (meso C), 128.94, 128.4, 124.34, 124.08 (C phenyl and phenoxy), 36.20 (C$_7$ and C$_8$ pyrrole).

Compound 75:
TPP(p-O-DEG-OH)$_3$: 5,10,15-tri(para-O-diethyleneglycoloxyphenyl)-20-phenylporphyrin:
UV-vis spectrum in CH$_2$Cl$_2$: λ$_{max}$, nm (ε L mmol$^{-1}$ cm$^{-1}$): 420 (436), 517 (16.4), 553 (10), 592 (5.1), 648.5 (5.2).
$^1$H NMR (CDCl$_3$), δ (ppm): 8.84 (m, 8H, pyrrole), 8.2 (dd, 2H, ortho-phenyl, J=7.7 and 2 Hz), 8.09 (t, 6H, ortho-phenoxy, J=8.6 Hz), 7.74 (m, 2H, meta-phenyl), 7.25 (t, 3H, meta-phenoxy, J=8.6 Hz), 7.24 (t, 3H, meta-phenoxy, J=8.6 Hz), 4.36 (m, 6H CH$_2$—O-phenyl), 4.01 (m, 6H, CH$_2$—OCH$_2$CH$_2$—O-phenyl), 3.86 (t, 6H, O—CH, CH$_2$—O—CH$_2$CH$_2$OH, J=4.4 Hz), 3.78 (t, 6H, O—CH$_2$CH$_2$OH, J=4.4 Hz).
$^{13}$C NMR (CDCl$_3$), δ (ppm): 158.47 (C$_4$ phenoxy), 142 (C$_1$ phenyl), 135.56 (C$_2$ phenoxy), 134.81 (C$_2$ phenyl and C$_1$ phenoxy), 131 (CH pyrrole), 127.66 (C$_4$ phenyl), 126.57 (C$_3$ phenyl), 119.9-119.8-119.71 (meso-C), 112.8 (C$_3$ phenoxy), 72.69 (HOCH$_2$), 69.76 (CH$_2$—OCH$_2$CH$_2$—O-phenyl), 67.63 (CH$_2$—O-phenyl), 61.89 (CH$_2$—OCH$_2$OH), Compound 74 (Protected):
TPP(p-O-TEG-S-oc-MannOAc)$_3$: 5,10,15-tri[para-10-S-(2',3',4',6'-tetraacetyl-α-D-thiomanosyloxy)-O-triethylene glycoloxyphenyl]-20-phenylporphyrin:
Yield 97%
UV-vis spectrum in CH$_2$Cl$_2$: λ$_{max}$, nm (ε L mmol$^{-1}$ cm$^{-1}$): 421 (423), 517.5 (16.5), 554 (10.4), 593 (5.3), 650 (6.2).

$^1$H NMR (CDCl$_3$), δ (ppm): 8.86 (m, 8H, pyrrole), 8.21 (dd, 2H, ortho-phenyl, J=6.4 and 2 Hz), 8.11 (d, 6H, ortho-phenoxy, J=8.3 Hz), 7.76 (m, 3H, meta and para-phenyl), 7.30 (d, 2H, meta-phenoxy, J=8.3 Hz), 5.39 (d, 6H, HC$_1$ and HC$_2$ "ose"), 5.33 (m, 3H, HC$_3$ "ose"), 5.31 (m, 3H, HC$_4$ "ose"), 4.41 (m, 3H, HC$_5$ "ose"), 4.43 (t, 6H, CH$_2$—O-phenyl, J=4.5 Hz), 4.34 (dd, 3H, HC$_{6a}$ "ose", J=12 and 5 Hz), 4.12 (dd, 3H, HC$_{6b}$ "ose", J=12 and 5 Hz), 4.06 (t, 6H, O—CH$_2$—(CH$_2$—O-phen), J=4.5 Hz), 3.86 (t, 6H, —O—CH$_2$—CH$_2$—O, J=4.5 Hz), 3.71-3.86 (m, 6H, —O—CH$_2$—CH$_2$—S), 3.76 (t, 6H, —O—CH$_2$—CH$_2$—O or —O—CH$_2$—CH$_2$—S, J=4.5 Hz), 2.96 (m, 6H, S—CH$_{2a}$), 2.83 (m, 6H, S—CH$_{2b}$), 2.18 (s, 9H, acetyl), 2.12 (s, 9H, acetyl), 2.03 (s, 9H, acetyl), 1.98(s, 9H, acetyl), −2.77 (s, 2 H, NH).

$^{13}$C NMR (CDCl$_3$), 6 (ppm): 170.6 (CO acetyl), 169.9 (CO acetyl), 169.8 (CO acetyl), 169.7 (CO acetyl), 158.6 (C$_4$ phenoxy), 142.3 (C$_1$ phenyl), 136 (C$_2$ phenoxy), 134.8 (C$_1$ phenoxy), 134.5 (C$_2$ phenyl), 131 (broad, CH pyrrole), 129 (C$_4$ phenyl), 127 (C$_3$ phenyl), 119.9-119.8 (meso-C), 112.8 (C$_3$ phenoxy), 82.9 (C$_1$ "ose"), 71.05 (C$_2$ "ose"), 70.9 (O—CH$_2$—CH$_2$—O), 70.6 (—O—CH$_2$—CH$_2$—O or —O—CH$_2$—CH$_2$—S), 70.5 (—O—CH$_2$—CH$_2$—S), 70 (O—CH$_2$—(CH$_2$—O-phen), 69.4 (C$_4$ "ose"), 69.1 (C$_5$ "ose"), 67.7 (CH$_2$—O-phen), 66.3 (C$_3$ "ose"), 62.45 (C$_6$ "ose"), 30.8 (S—CH$_2$), 20.95 (CH$_3$ acetyl), 20.8 (CH$_3$ acetyl), 20.7 (CH$_3$ acetyl), 20.65 (CH$_3$ acetyl).

Compound 74 (Deacetylation):
TPP(p-O-TEG-S-α-MannOH)$_3$: 5,10,15-tri(para-10-S-α-D-thiomanosyloxy-O-triethylene glycoloxyphenyl)-20-phenylporphyrin:

Yield 96%

UV-vis spectrum in MeOH/pyridine 24/1 v/v: $\lambda_{max}$, nm (ε L mmol$^{-1}$ cm$^{-1}$) 417.5 (318.8), 516 (14.5), 552 (19.9), 592 (5.5), 649 (5.8).

$^1$H NMR (pyridine d$_5$), δ (ppm): 9.16 (s, 4H, pyrrole), 9.12 (d, 2H, pyrrole, J=4.8 Hz), 9.06 (d, 2H, pyrrole, J=4.8 Hz), 8.37 (m, 2H, ortho-phenyl), 8.27 d, 6H, ortho or meta phenoxy, J=8.5 and 2.2 Hz), 7.79 (m, 3H, meta and para-phenyl), 7.45 (d, 6H, meta or ortho phenoxy, J=8.5 and 2.2 Hz), 6.02 (s, 3H, HC$_1$ "ose"), 4.71 (m, 3H, HC$_2$ "ose"), 4.68 (m, 6H, HC$_4$ and HC$_5$ "ose"), 4.60 (dd, 3H, HC$_{6a}$ "ose"), 4.55 (m, 3H, HC$_3$ "ose"), 4.42 (dd, 3H, HC$_{6b}$ "ose"), 4.44 (t, 6H, —CH$_2$—O-phen, J=4.5 Hz), 4.03 (t, 6H, O—CH$_2$—(CH$_2$—O-phen), J=4.5 Hz), 3.95-3.71 (m, 6H, O—CH$_2$—(CH$_2$S), 3.80 (t, 6H, O—CH$_2$CH$_2$—O—, J=4.5 Hz), 3.73 (t, 6H, O—CH$_2$CH$_2$—O—, J=4.5 Hz), 3.18 (m, 3H, S—CH$_{2a}$), 2.96 (m, 3H, S—CH$_{2b}$), −2.3 (s; 2H, NH).

$^{13}$C NMR (pyridine d$_5$), δ (ppm): 158.6 (C$_4$ phenoxy), 142.8 (C$_1$ phenyl), 136.3 (C$_1$ phenoxy and C$_2$ or C$_3$ phenoxy), 135 (C$_2$ phenoxy), 132 (broad, CH pyrrole), 128.4 (C$_4$ phenyl), 127.5 (C$_3$ phenyl), 120.8 (meso-C), 113.7 (C$_3$ or C$_2$ phenoxy), 86.9 (C$_1$ "ose"), 76.1 (C$_2$ "ose"), 73.7 (C$_4$ "ose"), 71.5 (—O—CH$_2$—CH$_2$—O or —O—CH$_2$—CH$_2$—S), 71.2 (—O—CH$_2$—CH$_2$—S), 70.8 (O—CH$_2$—CH$_2$—O), 70.3 (O—CH$_2$—(CH$_2$—O-phen), 69.6 (C$_5$ "ose"), 68.4 (CH$_2$—O-phen), 63.2 (C$_6$ "ose"), 30.9 (S—CH$_2$)

MALDI TOF spectrum for C$_{30}$H$_{96}$N$_4$O$_{24}$S$_3$: Calc. 1592.55; found: 1593.50 M+1.

The applicant has issued a pharmacologic study of the porphyrin derivatives according to the invention, which demonstrated very positive properties in the field of photodynamic antitumoral treatments and of antiviral photodynamic treatments. The main results for antitumoral effects are reported in Table B, showing the rate of photocytotoxicity. The higher the percentage, the higher the antitumnoral or antiviral effect.

Concerning the antitumoral activity, the compounds obtained by the inventors are active, under appropriate irradiation indicated towards tumoral cells in which these derivatives are able to accumulate.

A pharmacologic study has been made in vitro on cellular lines of human cancerous cells: KB cells, L-1210 cells, HT-29 cells, MCF-7 cells, FT-1 cells, RBY-79 (indifferently named Y-79) cells.

More precisely, concerning the KB cells (human buccal carcinoma cells), the method has been as follows. The porphyrin derivatives were dissolved in DMSO. The solution obtained is diluted in PBS containing Ca++ and Mg++ and 0,1% of glucose, at concentrations varying from 10 μM to 0,005 μM, then incubated 3 hours with a culture of the human cancerous KB cells line. The cellular cultures were then rinsed with a culture medium, then irradiated during 15 to 30 minutes by light source >550 un. The cells are afterwards put into culture medium for 18 hours, the rate of mortality was evaluated by colorimetric method at neutral red.

Concerning the HT29 cells, the method is as follows. Photodynamic activity of the glycoconjugated tetrapyrrolic macrocycles has been estimated using the viability of a human colic adenocarcinoma cell line HT29 (ATCC, HTB 38) after 24 h incubation with the tested compounds followed by visible light irradiation. HT29 cells were cultivated in Dulbecco's MEM supplemented with 10% fetal calf serum (FCS). Cells from log-phase culture were seeded in 24-microwell plates (1 mL-5×10$^4$ cells/well) and kept at 37° C. in a water-jacketed incubator for 2 days under an air/CO$_2$ atmosphere (5% CO$_2$). Tested compounds, in DMSO solution, were added under the minimum volume (5 μL) to reach a concentration ranging from 0.1 to 10 μg/mL. Controls cells received 5 μL of DMSO free of dye. Plates were incubated 24 h, then medium was removed and the cells were washed twice with phosphate buffered saline (PBS) before addition of fresh medium free of drug and irradiation with visible light using a home made "light box" giving a fluence of 3.8 mW/cm$^2$ on the whole visible spectrum. Irradiation with red light was carried out using the same device fitted with an orange filter (0% T at 520 nm and 80% T at 590 nm) leading to a fluence of 2 mW/cm$^2$.

Plates were reincubated for 3 days before evaluation of the cell survival using the MTT assay (T. Mosmann, "Rapid calorimetric assay for cellular growth and survival. Application to proliferation assays". J. Immunol. Methods 65,55-63,1983) using 30 min incubation with 100 μg well of 3-[4,5-dimethylthiazol-2-yl]-2,5-diphenyl tetrazolium bromide (MTT, Sigma). After removal of the medium, formazan crystals were taken up with 100 μL of DMSO and absorbance at 540 ni was measured with a Bio-Rad microplate reader (model 450); survival was expressed as % of untreated controls.

Concerning the antiviral activity the inventors have shown that cellular compounds of the invention are active, under irradiation at wave of about 600 nm, against the virus and in particular against retrovirus. The retrovirus are an important group of virus enveloped that use during their replication an enzyme of reverse transcription for converting an ARNm into ADN. The retrovirus include lentivirus, spumavirus, oncornavirus (type A, B, C, D, and virus with ARN tumour). These retrovirus are able to infect in particular human beings. Antiviral phototherapy has been developed in the last years in particular targeting retrovirus, as reminded in document FR 2,709,491.

A pharmacological study has been made since in vitro by the inventors relative to a virus of herpes simplex and of friend B. For instance the method has been as follows. The new compounds tested are dissolved in DMSO then diluted with PBS. Solutions at different concentrations of the compound are introduced in virus in a culture medium. The virus and the compound are incubated 45 min at 4° C. and in the dark. The viruses tested are irradiated 10 minutes at waves between 600 and 650 nm. The viruses are inoculated to cells sensitive to virus.

TABLE B

Photocytotoxicity of porphyrin derivatives

| Compound | Sugar | KB | Cytotoxicity L-1210 (no light) | Antitumoral | | | |
|---|---|---|---|---|---|---|---|
| | | | | HT 29 | MCF-7 | FT-1 | RBY-79 |
| 23 | Thio-β-gluose C3 | | 0% 10 µg/ml | 50% 6 µg/ml | | | 50% 3 µg/ml |
| 24 | Thio-α-mannose C3 | | 50% 14 µg/ml | 50% 4.6 µg/ml | | | 50% 6.5 µg/ml |
| 25 | Thio-β-glucose F4 | | 18% 10 µg/ml | inactive | | | inactive |
| 26 | Tio-β-glucose F4 | | 20% 10 µg/ml | 50% 2 µg/ml | | | 50% 3.3 µg/ml |
| 27 | Thio β-xylose F4 | | 50% 14 µg/ml | 50% 7.5 µg/ml | | | 50% 1.6 µg/ml |
| 28 | Thio β-xylose F4 | | 50% 9 µg/ml | 50% 3.7 µg/ml | | | 50% 1.7 µg/ml |
| 30 | Thio α-mannose F4 | | | | | | 90% 2 µg/ml |
| 31 | Thio α-mannose F4 | | | | | | 80% 2 µg/ml |
| 32 | Thio α-mannose F4 | | | | | | 95% 2 µg/ml |
| 33 | Thio α-mannose F4 | | | | | | 90% 2 µg/ml |
| 41 | β-lactose | | 0 | | | | |
| 42 | Porphyrine β-glucose | | Nd | | | | |
| 54 | Chlorine β-glucose | | | 0, A549, 0 | | Red 20% | |
| 55 | Chlorine β-glucose | | | Red, 0 A549, 10 | | Red 25% | |
| 58 | Chlorine β-glucose C2 | | Red, 0, A549 | | | Red 0 | |
| 60 | Porphyrine β-glucose | | A549, 20 | | | 0 | |
| 61 | Porphyrine β-glucose C2 | | Red, 0 A549, 0 | | | Red 0 | |
| 63 | β-glucose | | | | | | 37% 10 µg/ml white light |
| 64 | β-xylose | | 32% cytotoxicity at 10 µg/ml | 30% at 10 µg/ml | | | 50% at 7 µg/ml with light or not |
| 65 | β-glucose | | 16% cytotoxicity at 10 µg/ml | | | | 50% at 5 µg/ml with light or not |
| 66 | Thio-α-mannose | | 0% 10 µg/ml | 40% 10 µg/ml | | | 20% 10 µg/ml |
| 67 | α-mannose | | 50% 8 µg/ml | 50% at 1.5 µg/ml | | | 50% at 1.5 µg/ml, 80% at 2 µg/ml, 0% at 1 µg/ml |
| 68 | Thio-α-mannose | | 0% 10 µg/ml | 50% 4 µg/ml | | | 50% 1 µg/ml |

Other assays have been made and results are presented in the following tables C2 to C7. The activity of these tested compounds is compared to control reference compounds of table C1.

TABLE C1

| Compound | HT 29 IC$_{50}$ (μM) without light | HT 29 IC$_{50}$ (μM) with 2J/cm$^2$** | Y79 IC$_{50}$ (μM) without light | Y79 IC$_{50}$ (μM) With 2J/cm$^2$** |
|---|---|---|---|---|
| *Reference compounds* | | | | |
| Photofrin ® | Inactive for 10 μg/ml | 6 μg/ml (5.1)$^2$ $I_{Eff.} = <0.5$ | 4.6 μg/ml (3.9)$^1$ | 3 μg/ml (2.6)$^2$ $I_{Eff} = 0.67$ |
| TPP(p-OH)$_4$ | 7.75 ± 3 | 0.8 ± 1 $I_{Eff.} = 0.11$ | 4.7 ± 2.5 | 0.3 ± 1 $I_{Eff} = 0.06$ |
| TPP(p-O-β-GluOH)$_4$ | Inactif à 10 μM | | 7 ± 4 | 5.2 ± 4 $I_{Eff} = 0.74$ |
| TPP(p-OH)$_3$ | Inactive for 15 μM | 1.65 ± 0.07 $I_{Eff} < 0.1$ | >10 | 1.8 ± 0.1 $I_{Eff} < 0.1$ |
| TPP(p-O-β-GluOH)$_3$ | Inactive for 15 μM | 1.5 ± 0.2 $I_{Eff} < 0.1 =$ | >15 | 0.9 $I_{Eff} < 0.06$ |

TABLE C2

| Polyethylene glycol compounds | | | | |
|---|---|---|---|---|
| TPP(p-O-DEG-OH)$_3$ 75 | 6.5 | 4.3 $I_{Eff} = 0.66$ | 4.5 | 1.2 $I_{Eff} = 0.27$ |
| TPP(p-OC$_3$-S-α-MannOH)$_3$ 24 | 3.2 | 3.2 $I_{Eff} = 1$ | 7.5 | 4.7 $I_{Eff} = 0.62$ |
| TPP(p-O-DEG-O-α-Mann)$_3$$^3$ 67 | >10 | 0.7 ± 0.4 $I_{Eff} < 0.07$ | >10 | 0.3 ± 0.08 $I_{Eff} < 0.03$ |
| TPP(p-O-DEG-S-α-Mann)$_3$ 68 | >10 | 5.8 ± 3 $I_{Eff} < 0.2$ | 6 ± 2 | 1 ± 0.5 $I_{Eff} = 0.17$ |
| TPP(p-O-TEG-S-α-Mann)$_3$$^4$ 74 | 10.5 | 4.8 $I_{Eff} = 0.46$ | 11 ± 5 | 0.5 ± 0.3 $I_{Eff} = 0.05$ |

TABLE C3

| Fluorous and oxygenated compounds | | |
|---|---|---|
| TPPF$_4$(p-O-β-GluOH)$_4$ 63 | Inactive for 10 μM$^4$ | Inactive for 10 μM |

TABLE C4

| Fluorous and Sulfur compounds | | | | |
|---|---|---|---|---|
| TPP F$_4$(p-S-β-GluOH)$_4$ 25 | Inactive for 10 μM | | Inactive for 10 μM | 4 $I_{Eff} < 0.4$ |
| TPP F$_4$(p-S-β-GluOH)$_3$ 26 | 6.5 | 1.7 $I_{Eff} = 0.26$ | Inactive for 10 μM | 2.2 $I_{Eff} < 0.22$ |
| TPP F$_4$(p-S-β-XylOH)$_4$ 27 | Inactive for 10 μM | 5 $I_{Eff} < 0.5$ | Inactive for μM | 1 $I_{Eff} < 0.1$ |
| TPP F$_4$(p-S-β-XylOH)$_3$ 28 | Inactive for 10 μM | 2.6 $I_{Eff} < 0.26$ | Inactive for 10 μM | 1.2 $I_{Eff} < 0.12$ |
| TPP F$_4$(p-S-α-MannOH)$_4$ 29 | Inactive for 10 μM | 2.4 $I_{Eff} < 0.24$ | Inactive for 10 μM | 3.3 $I_{Eff} < 0.33$ |
| TPP F$_4$(p-S-α-MannOH)$_3$ 33 | Inactive for 10 μM | 1.7 | Inactive for 10 μM | 2.7 |

TABLE C5

| Sulfur benzyl compounds | | | | |
|---|---|---|---|---|
| TPP(p-CH$_2$-S-β-GluOH)$_4$ 65 | Inactive for 10 μM | 5.2 $I_{Eff} < 0.52$ | 4.7 | Inactive |
| TPP(p-CH$_2$-S-β-XylOH)$_4$ 64 | Inactive for 10 μM | 4.5 $I_{Eff} < 0.45$ | 3.8 | Inactive |
| TPP(p-CH$_2$-S-α-MannOH)$_4$ 66 | 21 | 10 $I_{Eff} = 0.5$ | 28 | 15 $I_{Eff} = 0.54$ |

TABLE C6

| Chlorines | | | | |
|---|---|---|---|---|
| m-THPC (Foscan ®) | >10 | 0.8 ± 0.3 $I_{Eff} < 0.08$ | >10 | 0.6 ± 0.03 $I_{Eff} < 0.06$ |
| TPC(m-OH)$_3$ 77-78 | 6.6 ± 0.9 | 1.5 ± 0.07 $I_{Eff} = 0.22$ | >10 | 0.6 ± 0.1 $I_{Eff} < 0.06$ |
| TPC(m-O-β-GluOH)$_4$ 54 | Inactive for 15 μM | 4.4 ± 0.1 $I_{Eff} < 0.3$ | 3.9 ± 0.1 | 3 ± 1.4 $I_{Eff} = 0.77$ |
| TPC(m-O-β-GluOH)$_3$ 55 | Inactive for 15 μM | 5.7 ± 3 $I_{Eff} < 0.38$ | 8 ± 7 | 3.7 ± 1.8 $I_{Eff} = 0.46$ |

TABLE C7

| Other compounds | | | | |
|---|---|---|---|---|
| TPP(p-OC$_3$-S-β-GluOH)$_3$ | 13 | 11 | Inactive for | 6.5 |
| 23 | | $I_{Eff}$ = 0.85 | 10 μM | $I_{Eff}$ < 0.65 |

[1]$I_{Eff}$ Efficiency Index defined as IC$_{50}$ with light/IC$_{50}$ without light
**Irradiation with filter (0% T at 520 nm and 80% T at 590 nm), 3.5 mW/cm$^2$, 10 min.
[2]Estimated concentration for mean molecular weight of photofrin ®: 1178.55 dimer form
[3]—O-DEG = —O—CH$_2$CH$_2$—O—CH$_2$CH$_2$—
[4]—O-TEG = —O—CH$_2$CH$_2$—O—CH$_2$CH$_2$—O—CH$_2$CH$_2$—

Table B shows in particular that some compounds are cytotoxic only without light (L1210), whereas the compounds of the invention are active when they are activated by light: for instance compounds 24 and 26 are active contrarily to compound 25. Thus the inventors have done efforts to synthetise and identify active compounds, which are not obvious to the one skilled in the art considering that compound that may look similar exhibit very different activities.

Table C1 shows the cytotoxic effect of reference compounds which are known in the state of the art, and are considered as control compounds for the tested compounds of the invention.

Tables C2 to C7 show the results of tested compounds. Columns HT29 and Y79 (=RBY79), without light, correspond to the cytotoxic activity. Column L1210 corresponds to the cytostatic activity.

The efficacity rate $I_{Eff}$ is defined as the ratio of the photocytotoxic activity under a cytotoxic activity.

$I_{Eff}$=IC$_{50}$ with light/IC$_{50}$ without light

Thus, the less $I_{Eff}$ is, the more interesting is the compound.

The inventors have made the main following remarks.

The compound photofrin® is cytotoxic at more than 3,9 μM, for the Y79 cells.

The reference compound TPP(p-OH)$_4$ is a cytotoxic for the HT29 and Y79 cells.

The compounds TPP(p-OH)$_4$, 24, 26, m-THPC (Foscan®) and TPC(m-OH)$_3$ are cytotoxic for HT29.

The compounds Photofrin, TPP(p-OH)$_4$, 64, 65, m-THPC (Foscan®), 54 and 55 are cytotoxic for Y79.

Among all the compounds presented in the tables:
Compound 67 exhibits a ratio $I_{Eff}$<0.1 for HT29 and <0.03 for Y79, and thus may be useful.

Compound 68 has a $I_{Eff}$=0,09 for Y79, a little bit less than for compound 67.

Compound 68 is not altered in vitro and thus might be very useful in vivo.

The new compound called TPP(p-O-TEG-S-α-MannOH)$_3$, has an $I_{Eff}$<0,03 for Y79, which is as good as for compound 64 indicating that this compound is a good candidate.

The inventors have noticed the effects of the sugars and of the glycol chain in the compounds polyethylene glycol, 24, 67, 68, TPP (p-O-TEG-S-α-MannOH)$_3$ and TPP(p-O-DEG-OH)$_3$.

The compound 24 is cytotoxic for HT29 and Y79, but less phototoxic for these cells.

The replacement of a monoethyleneglycol (compound 24), by a diethyleneglycol (compound 67), highly increases the ratio $I_{Eff}$, by highly decreasing the cytotoxicity and increasing the phototoxic activity.

Furthermore, compound TPP(p-O-DEG-OH)$_3$, non glycosylated analogous compound of compound 67, is totally inactive, showing the effect of sugars on the biological activities.

Besides the compounds 27 and 28 show a $I_{Eff}$<0.1 for Y79.

The chlorin TPC(m-OH)$_3$, trihydroxylated analogous compound of Foscan® shows a $I_{Eff}$<0.05 for Y79.

The compound 55 is a mixture of the two position isomers, in proportion 50/50 (see the RMN spectra).

The invention also relates to a method of screening of porphyrin compounds useful in photodynamic therapy comprising adding the tested compound to cells to inactivate, photoactivating said compound, and measuring the inactivation of cells.

The invention also relates to the use of a compound obtained by the method of screening above, for the preparation of a drug useful in photodynamic therapy.

The one skilled in the art has now with the present application sufficient data (the compounds to test and the accurate testing protocol which allows to measure the biological activity) to identify the efficient compounds without undue experiment.

The invention also relates to a method of treatment using any of the porphyrin compounds described in the present application.

It will be noted that the compounds of the invention contain at last one chiral centre and thus may exist in various stereoisomeric forms. If desired, such stereoisomers, including enantiomers, may be separated using techniques standard in the art; however, racemic mixtures or mixtures containing more than one diastereomer may also be used. The effect of some compounds tested is related to the D/L isomery at the Carbon 5, and the α/β isomery at the carbon 1. Particularly advantageous isomery is mentioned in table A and B. The invention also relates to mono or poly saccharides from which one or several —OH are protected.

If desired, the compounds of the invention can be prepared in metallated forms by treating the tetrapyrrole-type nucleus with an appropriate ion such as magnesium ion, zinc ion, stannous ion and the like, to obtain a metal complex. The metal ion may also be a radiolabel. Generally, the metal ion is inserted using the appropriate salts under conditions standard in the art. For example, zinc ion can be introduced by treating the compound with zinc acetate in 1:1 methylene choride:methanol.

The compounds may also contain label, including radioisotopes, chromophores, and fluorescent labels. Radioisotope labelling is generally useful when the compounds are to be followed in vivo or used to label specific moieties. Useful cationic moieties that are radioisotopes include technetium, gallium and indium. In addition, radioisotopes of heteroatoms, such as $^{131}$I or $^{32}$P, in the molecule itself, or inclusion of $^{14}$C may be used to label the molecule.

The compounds of the invention may be coupled, if desired, to a targeting agent which will direct the molecule to a specific tissue or organ. Such targeting agents include antibodies, receptors, receptor-ligands and the like. Linkage of the targeting agent to the compound, in a "conjugated form", is conducted using standard techniques reminded in WO90/15059.

The compounds of the invention may be formulated in a variety of ways for pharmaceutical use. Generally speaking, such formulations include any excipients, stabilizers, emulsifying agents, osmotic agents, solubilizing agents and the like, that are recognized as useful to deliver photosensitizer compounds to the body whether topically or internally in any way such as by intravenous, intraperitoneal, or intramuscular injection, transmucosally, orally, transdermally by way of skin patches, salves and gels, and such. Liposomal formulations, as recognized in the art, represent an advantageous form of formulation, including formulations with phosphatidyl serine, phosphatidyl glycerol, phosphatidyl choline, and the like. Additionally, it will be recognized that functional groups are typically added to the macrocycles of the present invention to facilitate their storage, preparation, solubility, and physiological utility. Generally, reference may be made to Remington's Pharmaceutical Sciences, Mack Publishing Company, Easton, Pa., latest addition. Additional information concerning generally acceptable formulations is provided in U.S. Pat. Nos. 5,095,030; 5,171,749; 5,776,966; 5,789,433; 4,512,762; 4,566,636; 5,399,583; 4,920,143, pertaining to photosensitizers for pharmaceutical use.

The compounds of the invention may generally be used for all of the therapeutic applications for which photosensitizer compounds have been recognized, as mentioned for example in the cited patents. As is recognized by medical practitioners, dosages vary considerably based on the mode of administration, formulation, condition of the patient, condition to be treated, and the like. For systemic administration, dosages on the order of 10 µg/kg to 100 mg/kg, preferably 100 µg/kg to 10 mg/kg may be preferred. With respect to topical administrations, suitable compositions may range from about 1 to 10% of the composition, or greater or lesser, depending upon the application, as would be recognized in the art.

The invention claimed is:
1. Porphyrin compound of formula 1

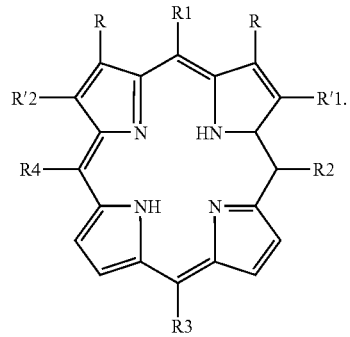

And the metallated and/or labelled and/or conjugated forms thereof wherein,
a) R1=X1-R5, R2=X1-R6, R3=X1-R7, R4=X1-R8
Wherein X1=

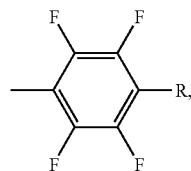

and
a.1) at least one group among R5, R6, R7, R8 is a group A=S-D-Sugar OH, the other group(s) being the atom F, the sugar being a mono, a bi or a polysaccharide advantageously chosen in the group consisting of maltose, lactose, mannose, xylose, glucose, a.2) at least one group among R5,R6,R7,R8 is A'=O-sugar, the other groups being the atom F, the sugar being a mono or a polysaccharide advantageously chosen in the group consisting of galactose, mannose, xylose, glucose, or
b) R2=-Y1-H and R1=R3+=R4=Y1-R9 where Y1=

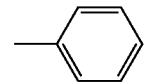

and is substituted in ortho, meta or para, and
  b.1) R9=O-CH2-CH2-CH2-S-sugar, the sugar being a mono or a polysaccharide advantageously chosen in the group consisting of glucose and mannose, or
  b.2) R9=O—CH2-CH2-Y—CH2-CH2-X-Sugar, or R9=O—CH2-CH2-Y—CH2-CH2-Y—CH2-CH2-X-Sugar, wherein X=O,S,-CH2- and Y=—O—,—CH2-, or
  b.3) R9=CH2-X-Sugar where X=O,S,CH2, the sugar being a mono, a di or a polysaccharide advantageously chosen in the group consisting of maltose, lactose, mannose, xylose, glucose, galactose, or
c) R1=R2=R3=R4=-Y1-B where Y1 is

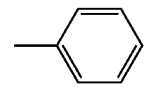

and is substituted in para, and B=(CH2)n-S-sugar, the sugar being chosen in the group consisting of mannose, and xylose, glucose, and n=1 or 2,
or
d) R1=C-A4, R2=C—A3, R3=C—A2, R4=C—A1 where each substituent C is

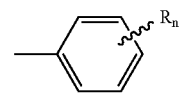

and is a m-hydroxyphenyl or p-hydroxyphenyl and
  d.1) at least two groups among A1,A2,A3,A4 are the group O-glucose OH, the other being the atom H, or
  d.2) at least two groups among A1,A2,A3,A4 are the group O—CH2CH2CH2—O—D-glucose OH, the others being the atom H
  and where R=R'1=R'2=H in a),b),c),d) or
e) R1=R2=R3=H, R=R'1=R'2=CH2CH3 and R4=D-sugar where
D=
the

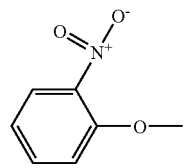

polysaccharide advantageously chosen in the group consisting in glucose, maltose, mannose, xylose, or R1=R2=R3=R4=H, R=CH3,R'1=D—H,R'2=D-sugar the sugar being a mono or a polysaccharide advantageously chosen in the group consisting of maltose, mannose, xylose, lactose and higher polysaccharides.

2. Compound according to claim 1 characterized in that it is chosen in the group consisting of
a) R5=R6=R7=R8=S-Sugar OH
b) R5=R7=R8=S-Sugar OH and R6=F
c) R6=R8=S-Sugar OH and R5=R7=F
d) R7=R8=S-Sugar OH and R5=R6=F
where Sugar+(glucose or manrtose or xylose).

3. Compound according to claim 2, characterized in that it is chosen in the group consisting of
a) R5=R6=R7=R8=S-Sugar OH
b) R5=R7=R8=S-Sugar OH and R6=F where Sugar=xylose.

4. Compound according to claim 2, characterized in that it is chosen in the group consisting of
a) R5=R7=R8=S-Sugar OH and R6=F
b) R6=R8=S-Sugar OH and R5=R7=F
c) R7=R8=S-Sugar OH and R5=R6=F where Sugar=α-mannose.

5. Compound according to claim 1, characterized in that it is chosen in the group consisting of
a) A1=A2=A3=A4=O-glucose OH
b) A1=A2=A3=O-glucose OH, A4=H
c) A1=A2=O-glucose OH, A3=A4=H.

6. Porphyrin compound of formula 1

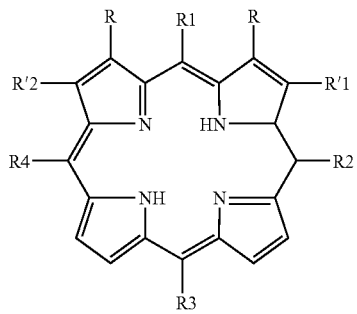

and the metallated and/or labelled and/or conjugated forms thereof wherein,
a) R1=X1-R5, R2=X1-R6, R3=X1-R7, R4=X1-R8 wherein X1=

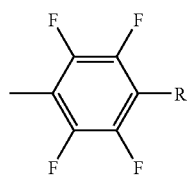

and
a.1) two or three groups among R5,R6,R7,R8 are a group A=S—D-Sugar OH, the other groups being the atom F, the sugar being a mono, a bi or a polysaccharide advantageously chosen in the group consisting of maltose, lactose, mannose, xylose, glucose, a.2) two or three groups among R5,R6,R7,R8 are A'=O-sugar, the other groups being the atom F, the sugar being a mono or a polysaccharide advantageously chosen in the group consisting of galactose, mannose, xylose, glucose, or
b) R2=-Y1-H and R1=R3=R4=Y1-R9 where Y1=

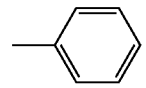

and is substituted in ortho, meta or para, and
b.1) R9=O—CH2-CH2-CH2-S-sugar, the sugar being a mono or a polysaccharide advantageously chosen in the group consisting of glucose and mannose, or
b.2) R9O—CH2CH2-Y—CH2CH2-X-Sugar, or R9=O—CH2-CH2-Y—CH2-CH2-Y—CH2-CH2-X-Sugar, wherein X=O, S, —CH2 and Y=—O—, —CH2-,
or
b.3) R9=CH2-X-Sugar where X=O, S, CH2, the sugar being a mono, a di or a polysaccharide advantageously chosen in the group consisting of maltose, lactose mannose, xylose, glucose, galactose,
or
c) Two or three groups among R1=R2=R3=R4=Y1-B where Y1 is

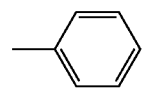

and is substituted in para, and B=(CH2)n-S-sugar, the sugar being chosen in the group consisting of mannose, and xylose, glucose, and n=1 or 2,
or
d) R1=C—A4, R2=C—A3, R3=C—A2, R4=C—A1 where each substituent C is

and is a m-hydroxyphenyl or p-hydroxyphenyl and
d.1) two or three groups among A1,A2,A3,A4 are the group O—CH2CH2CH2-O—D-glucoseOH, the others being the atom H
and where R=R'1=R'2=H in a), b), c), d).

7. Porphyrin compound characterized in that it is a polyethylene glycol compound chosen among TPP(p-OC3—S-α-MannOH)3, TPP(p-O-DEG-O-α-Mann)3, TPP(p-O-DEG-S-α-Mann)3, TPP(p-O-TEG-S-α-MannOH)3, TPP(p-O-DEG-OH)3.

8. Porphyrin compound, characterized in that it is the fluorous and oxygenated compound TPPF$_{-1}$(p-O-β-GluOH)$_4$.

9. Porphyrin compound characterized in that it is a fluorous and sulphur compound chosen among TPP F$_4$(p-S-β-GluOH)$_3$, TPP F$_4$(p-S-β-XylOH)$_4$, TPP F$_4$(p-S-β-XylOH)$_3$, TPP F$_4$(p-S-α-MannOH)$_4$ and TPP F$_4$(p-S-α-MannOH)$_3$.

10. Porphyrin compound characterized in that it is a sulphur benzyl compound chosen among TPP(p-CH$_2$—S-β-GluOH)$_4$, TPP(p-CH$_2$—S-β-XylOH)$_4$ and TPP(p-CH$_2$—S-α-MannOH)$_4$.

11. Porphyrin compound characterized in that it is the TPP(p-OC$_3$—S-β-GluOH)$_3$.

12. A pharmaceutical composition which comprises an effective amount of the compound as in any one of claims 1 to 10 and 11 in admixture with at least one parmaceutically acceptable excipient.

13. A method of treating retinoblastoma comprising:
preparing a drug comprising an effective amount of a compound selected from the group consisting of Photofrin and Foscan;
contacting a retinoblastoina with the drug comprising an effective amount of the compound; and
irradiating the retinoblastoma with light at a wavelength absorbed by the compound.

14. A method in vitro or in vivo to photosensitize, destroy or impair the functioning of target biological material which comprises contacting said target with an effective amount of a compound as in any one of claim 1 to 5 and irradiating said target with light at a wavelength absorbed by said compound.

15. The method of claim 14 wherein the biological material is one of a virus, tuxnoral cells, a bacteria, and tumorous tissues.

16. A method of screening of porphyrin compounds of claim 1 or 6 useful in photodynamic therapy comprising adding the tested compound to cells to inactivate, photoactivating said compound, and measuring the inactivation of cells.

17. A method in vitro or in vivo to photosensitize, destroy or impair the functioning of target biological materials comprising;
contacting a target biological material with an effective amount of a compound according to the method of claim 16; and
irradiating the target biological material with light at a wavelength absorbed by the compound.

* * * * *

UNITED STATES PATENT AND TRADEMARK OFFICE
CERTIFICATE OF CORRECTION

PATENT NO.         : 7,371,742 B2
APPLICATION NO. : 10/484529
DATED                  : May 13, 2008
INVENTOR(S)       : Grierson et al.

It is certified that error appears in the above-identified patent and that said Letters Patent is hereby corrected as shown below:

In column 3, line 24, on the right side of the depicted figure please delete "R," and insert -- R --.

In column 6, line 29, please delete "a" and insert -- α --.

In column 49, please delete the two figures and insert one figure that depicts the compound entirely as one entity. i.e. the first figure attached to the second figure to make a complete compound.

In column 63, line 31, please delete "($1.10^{-4}$ mole)" and insert -- ($1.5\ 10^{-4}$ mole) --.

In column 65, line 41, please delete "$^3$C" and insert -- $^{13}$C --.

In column 67, line 7, please delete "WV" and insert -- UV --.

In column 68, line 22, please delete "8 (ppm)" and insert -- δ (ppm) --.

In column 68, line 28, please delete "8 (ppm)" and insert -- δ (ppm) --.

In column 68, line 60, please delete "WV" and insert -- UV --.

In column 69, line 8, please delete "8 (ppm)" and insert -- δ (ppm) --.

In column 69, line 20, please delete "$N_{4O24}$" and insert -- $N_4O_{24}$ --.

In column 70, line 12, please delete "UW" and insert -- UV --.

In column 70, line 62, please delete "TPP(p-O-TEG-S-oc-MannOAc)$_3$" and insert -- TPP(p-O-TEG-S- α-MannOAc)$_3$ --.

UNITED STATES PATENT AND TRADEMARK OFFICE
CERTIFICATE OF CORRECTION

PATENT NO. : 7,371,742 B2
APPLICATION NO. : 10/484529
DATED : May 13, 2008
INVENTOR(S) : Grierson et al.

It is certified that error appears in the above-identified patent and that said Letters Patent is hereby corrected as shown below:

In column 71, line 16, please delete "6 (ppm)" and insert -- $\delta$ (ppm) --.

In column 72, line 51, please delete "540 ni" and insert -- 540 nm --.

In column 73-74, compound 41, please delete "0" under Cytotoxicity L-1 2 1 0 (no light) and insert -- 0 -- under KB.

In column 73-74, compound 42, please delete "Nd" under Cytotoxicity L-1210 (no light) and insert -- Nd -- under KB.

In column 75, Table C2, line 33, please delete "TPP(p-O-DEG-O- $\alpha$-Mann)$_3^3$" and insert -- TPP(p-O-$\underline{DEG_3}$-O- $\alpha$-Mann)$_3$ --.

In column 75, table C2, please delete "TPP(p-O-TEG-S- $\alpha$ -Mann)$^4_3$" and insert -- TPP(p-O-TEG$_4$-S- $\alpha$ -Mann)$_3$ --.

In column 79, line 58, right portion of the 2$^{nd}$ figure please delete "R," and insert -- R --.

In column 81, claim 1, line 2, please delete "in glucose" and insert -- of glucose --.

In column 81, claim 2, line 13, please delete "manrtose" and insert -- mannose --.

In column 82, claim 6, line 18, please delete "R9O-CH2CH2-Y-CH2CH2-X-Sugar" and insert -- R9=O-CH2-CH2-Y-CH2-X-Sugar --.

In column 82, claim 6, line 26, please delete "lactose" and insert -- lactose, --.

UNITED STATES PATENT AND TRADEMARK OFFICE
CERTIFICATE OF CORRECTION

PATENT NO.         : 7,371,742 B2
APPLICATION NO.    : 10/484529
DATED              : May 13, 2008
INVENTOR(S)        : Grierson et al.

It is certified that error appears in the above-identified patent and that said Letters Patent is hereby corrected as shown below:

In column 82, claim 8, line 61, please delete "$TPPF_{-1}(p\text{-}O\text{-}\beta\text{-}GluOH)_4$" and insert -- $TPPF_4(p\text{-}O\text{-}\beta\text{-}GluOH)_4$ --.

In column 83, claim 13, line 15, please delete "retinoblastoina" and insert -- retinoblastoma --.

Signed and Sealed this

Seventh Day of April, 2009

JOHN DOLL
*Acting Director of the United States Patent and Trademark Office*